(12) United States Patent
Holland et al.

(10) Patent No.: US 10,324,311 B2
(45) Date of Patent: Jun. 18, 2019

(54) VISIBLE-LIGHT PHOTOINITIATORS AND USES THEREOF

(71) Applicant: Novartis AG, Basel (CH)

(72) Inventors: Troy Vernon Holland, Suwanee, GA (US); Frank Chang, Cumming, GA (US); Ryan DeSousa, Atlanta, GA (US)

(73) Assignee: Novartis AG, Basel (CH)

( * ) Notice: Subject to any disclaimer, the term of this patent is extended or adjusted under 35 U.S.C. 154(b) by 326 days.

(21) Appl. No.: 15/168,697

(22) Filed: May 31, 2016

(65) Prior Publication Data

US 2016/0357031 A1 Dec. 8, 2016

Related U.S. Application Data

(60) Provisional application No. 62/169,722, filed on Jun. 2, 2015.

(51) Int. Cl.

| | | |
|---|---|---|
| *G02C 7/10* | (2006.01) |
| *B29D 11/00* | (2006.01) |
| *C08F 2/48* | (2006.01) |
| *C08F 2/50* | (2006.01) |
| *G02B 1/04* | (2006.01) |
| *C07F 7/30* | (2006.01) |
| *C07F 9/09* | (2006.01) |
| *C08F 26/06* | (2006.01) |
| *G02C 7/04* | (2006.01) |
| *C08F 220/54* | (2006.01) |
| *B29K 83/00* | (2006.01) |
| *B29K 105/00* | (2006.01) |

(52) U.S. Cl.
CPC ........ *G02C 7/108* (2013.01); *B29D 11/00038* (2013.01); *B29D 11/00134* (2013.01); *B29D 11/00519* (2013.01); *C07F 7/30* (2013.01); *C07F 9/098* (2013.01); *C08F 2/48* (2013.01); *C08F 2/50* (2013.01); *C08F 26/06* (2013.01); *G02B 1/04* (2013.01); *G02B 1/043* (2013.01); *G02C 7/049* (2013.01); *B29K 2083/00* (2013.01); *B29K 2105/0061* (2013.01); *B29K 2995/0062* (2013.01); *C08F 220/54* (2013.01)

(58) Field of Classification Search
CPC ........ B29D 11/00038; B29D 11/00134; B29D 11/00519; G02C 7/108; G02C 7/049; G02B 1/04; G02B 1/043; C08F 2/48; C08F 2/50; C08F 26/06; C07F 7/30; C07F 9/098

See application file for complete search history.

(56) References Cited

U.S. PATENT DOCUMENTS

| | | |
|---|---|---|
| 3,162,676 A | 12/1964 | Goldberg |
| 3,299,173 A | 1/1967 | Roselli |
| 4,444,711 A | 4/1984 | Schad |
| 4,460,534 A | 7/1984 | Boehm |
| 4,528,311 A | 7/1985 | Beard |
| 4,612,358 A | 9/1986 | Besecke |
| 4,716,234 A | 12/1987 | Dunks |
| 5,508,317 A | 4/1996 | Mueller |
| 5,583,163 A | 12/1996 | Mueller |
| 5,665,840 A | 9/1997 | Poehlmann |
| 5,712,356 A | 1/1998 | Bothe |
| 5,789,464 A | 8/1998 | Mueller |
| 5,843,346 A | 12/1998 | Morrill |
| 5,849,810 A | 12/1998 | Mueller |
| 5,849,841 A | 12/1998 | Muehlebach |
| 5,894,002 A | 4/1999 | Boneberger |
| 6,165,408 A | 12/2000 | Steinmann |
| 6,221,303 B1 | 4/2001 | Steinmann |
| 6,303,687 B1 | 10/2001 | Mueller |
| 6,472,489 B1 | 10/2002 | Stockinger |
| 6,479,587 B1 | 11/2002 | Stockinger |
| 6,492,478 B1 | 12/2002 | Steinmann |
| 6,627,124 B1 | 9/2003 | Herbrechtsmeier |
| 6,800,225 B1 | 10/2004 | Hagmann |
| 7,384,590 B2 | 6/2008 | Kelly |
| 7,387,759 B2 | 6/2008 | Kelly |
| 7,605,190 B2 | 10/2009 | Moszner |
| 7,977,430 B2 | 7/2011 | Devlin |
| 8,088,313 B2 | 1/2012 | Hagmann |
| 8,153,703 B2 | 4/2012 | Laredo |

(Continued)

FOREIGN PATENT DOCUMENTS

| | | |
|---|---|---|
| EP | 0958315 B1 | 6/2001 |
| EP | 0932635 B1 | 7/2001 |

(Continued)

OTHER PUBLICATIONS

Ballistreri et al., Selective and mild oxidation of thiols to sulfonic acids by hydrogen peroxide catalyzed by methyltrioxorhenium, Elsevier Ltd., Tetrahedron Letters, 49, 2008, pp. 3291-3293.

Castel et al., New (Diarylgermyl)lithiums, American Chemical Society, Organometallics, vol. 9, No. 1, 1990, pp. 205-210.

De Groot et al., Hydrophilic Polymeric Acylphospine Oxide Photoinitiators/Crosslinkers for in Vivo Blue-Light Photopolymerization, American Chemical Society, Biomacromolecules, vol. 2, No. 4, 2001, pp. 1271-1278.

Ganster et al., New Photocleavable Structures. Diacylgermane-Based Photoinitiators for Visible Light Curing, American Chemical Society, Macromolecules, vol. 41, No. 7, 2008, pp. 2394-2400.

Ikeda et al., Molecular Weight Dependence of Antibacterial Activity in Cationic Disinfectants, Journal of Bioactive and Compatible Polymers, vol. 5, 1990, pp. 31-41.

(Continued)

*Primary Examiner* — Mathieu D Vargot
(74) *Attorney, Agent, or Firm* — Jian Zhou

(57) ABSTRACT

Described herein are acyl germanium photoinitiator for cost-effective and time-efficient method for producing UV-absorbing contact lenses capable of blocking ultra-violet ("UV") radiation and optionally (but preferably) violet radiation with wavelengths from 380 nm to 440 nm, thereby protecting eyes to some extent from damages caused by UV radiation and potentially from violet radiation. This invention also provides a method for making UV-absorbing contact lenses made by using an acyl germanium photoinitiator of the invention.

20 Claims, No Drawings

(56) References Cited

U.S. PATENT DOCUMENTS

| | | | |
|---|---|---|---|
| 8,232,326 | B2 | 7/2012 | Laredo |
| 9,103,965 | B2* | 8/2015 | Chang .................. C07F 7/0849 |
| 9,315,669 | B2* | 4/2016 | Holland .................. C08L 83/04 |
| 2004/0082680 | A1 | 4/2004 | Phelan |
| 2005/0113549 | A1 | 5/2005 | Devlin |
| 2008/0076847 | A1 | 3/2008 | Moszner |
| 2008/0277814 | A1 | 11/2008 | Moszner |
| 2015/0080490 | A1 | 3/2015 | Burtscher et al. |
| 2015/0094393 | A1 | 4/2015 | Holland |

FOREIGN PATENT DOCUMENTS

| | | |
|---|---|---|
| EP | 0961941 B1 | 4/2002 |
| WO | 00/31150 A1 | 6/2000 |
| WO | 2015/048279 A1 | 4/2015 |

OTHER PUBLICATIONS

Lascelles et al., Latex Syntheses Using Novel Tertiary Amine Methacrylate-Based Macromonomers Prepared by Oxyanionic Polymerization, American Chemical Society, Macromolecules, vol. 32, No. 8, 1999, pp. 2462-2471.

Majima et al., Phenyl-2,4,6-trimethylbenzoylphosphinates as water-soluble photoinitiators, Makromolekulare Chemie, 192 (10), 1991, pp. 2307-2315.

G. Margomenou-Leonidopoulo, Thermal Behavior of Some Long-Chain Dl-n-Dodecyl Quaternary Ammonium Salts, Elsevier Science Publishers, Thermochimica Acta, 134, 1988, pp. 49-54.

Menard et al., Angiotensin Converting Enzyme Inhibitors. (Mercaptoaroyl)amino Acids, American Chemical Society, Journal of Medicinal Chemistry, 1985, vol. 28, No. 3, pp. 328-332.

Moszner et al., Benzoylgermanium Derivatives as Novel Visible-Light Photoinitiators for Dental Composites, Macromolecular Materials and Engineering, 2009, 294, pp. 877-886.

Moszner et al., Benzoyl germanium Derivatives as Novel Visible Light Photoinitiators for Dental Materials, Academy of Dental Materials, Elsevier Ltd., 2008, 24, pp. 901-907.

Neshchadin et al., Acylgermanes: Photoinitiators and Sources for Ge-Centered Radicals. Insights into their Reactivity, American Chemical Society, Journal of the American Chemical Society, 2013, 135, pp. 17314-17321.

Tehfe et al., Bis(germyl)ketones: Toward a New Class of Type I Photoinitiating Systems Sensitive Agove 500 nm?, Macromolecular Rapid Communications, 2010, 31, pp. 473-478.

Ullrich et al., Photoinitiators With Functional Groups. IX. Hydrophilic Bisacylphosphine Oxides for Acidic Aqueous Formulations, Wiley Periodicals, Journal of Polymer Science: Part A: Polymer Chemistry, vol. 44, 2006, pp. 1686-1700.

Umeda et al., Polymeric Phospholipid Analogues 14, The Convenient Preparation of a Vinyl Monomer Containing a Phospholipid Analogue, Makromol. Chem., Rapid Commun. 3, No. 7, Jul. 1982, pp. 457-459.

Zervas et al., On Cysteine and Cystine Peptides. II. S-Acylcysteines in Peptide Synthesis, Contribution from the Laboratory of Organic Chemistry, University of Athens, Greece, vol. 85, 1963, pp. 1337-1341.

* cited by examiner

VISIBLE-LIGHT PHOTOINITIATORS AND USES THEREOF

This application claims the benefits under 35 USC § 119 (e) of U.S. provisional application No. 62/169,722 filed 2 Jun. 2015, incorporated by reference in its entirety.

This invention is related to visible-light photoinitiators and their uses for producing contact lenses capable of blocking ultra-violet ("UV") radiation and optionally (but preferably) violet radiation with wavelengths from 380 nm to 440 nm, thereby protecting eyes to some extent from damages caused by UV radiation and potentially by high energy violet light (HEVL).

BACKGROUND

Most commercially-available non-silicone hydrogel contact lenses are produced according to a conventional cast molding technique involving use of disposable plastic molds and a mixture of vinylic monomers and crosslinking agents. There are several disadvantages with the conventional cast-molding technique. For example, a traditional cast-molding manufacturing process often includes lens extraction in which unpolymerized monomers must be removed from the lenses by using an organic solvent. Use of organic solvents can be costly and is not environmentally friendly. In addition, disposable plastic molds inherently have unavoidable dimensional variations, because, during injection-molding of plastic molds, fluctuations in the dimensions of molds can occur as a result of fluctuations in the production process (temperatures, pressures, material properties), and also because the resultant molds may undergo non-uniformly shrinking after the injection molding. These dimensional changes in the mold may lead to fluctuations in the parameters of contact lenses to be produced (peak refractive index, diameter, basic curve, central thickness etc.) and to a low fidelity in duplicating complex lens design.

The above described disadvantages encountered in a conventional cast-molding technique can be overcome by using the so-called Lightstream Technology™ (CIBA Vision), which involves (1) a lens-forming composition being substantially free of monomers and comprising a substantially-purified, water-soluble prepolymer with ethylenically-unsaturated groups, (2) reusable molds produced in high precision, and (3) curing under a spatial limitation of actinic radiation (e.g., UV), as described in U.S. Pat. Nos. 5,508,317, 5,583,163, 5,789,464, 5,849,810, 6,800,225, and 8,088,313. Lenses produced according to the Lightstream Technology™ can have high consistency and high fidelity to the original lens design, because of use of reusable, high precision molds. In addition, contact lenses with high quality can be produced at relatively lower cost due to the short curing time, a high production yield, and free of lens extraction and in an environmentally friendly manner because of use of water as solvent for preparing lens formulations.

However, the Lightstream Technology™ has not been applied to make UV-absorbing contact lenses, largely because of the lack of water-soluble photoinitiator which can efficiently initiate curing (polymerization) of an aqueous lens formulation using a visible light having a wavelength from 380 to 460 nm. Examples of known efficient visible-light photoinitiators include 2,4,6-trimethylbenzoyldiphenylphosphine oxide (TPO), 2,4,6-trimethylbenzoylethoxyphenylphosphine oxide (TPO-L), and bis(2,4,6-trimethylbenzoyl)phenylphosphine oxide (BAPO), acylgermanium compounds described in U.S. Pat. No. 7,605,190 (herein incorporated by reference in its entirety). But, those available photoinitiators are insoluble in water and cannot be used in the production of contact lenses from an aqueous lens formulation according to the Lightstream Technology™. Some attempts have been made to prepare more hydrophilic phosphine oxide photoinitiators (Majima, Tetsuro; Schnabel, W.; Weber, W. *Makromolekulare Chemie* 1991, 192(10), 2307-15; De Groot, J. H.; et. al. *Biomacromolecules* 2001, 2, 1271). The phosphine oxide photoinitiators reported in those studies either have a limited solubility in water or have a much reduced efficiency in initiating polymerization (i.e., prolonging the cure times).

Therefore, there are still needs for a new water-soluble photoinitiator that is active and efficient in curing an aqueous lens formulation in wavelengths from 390 to 500 nm and for making UV-absorbing contact lenses from an aqueous lens formulation according to the Lightstream Technology™.

SUMMARY

In one aspect, the invention provides an acyl germanium photoinitiator of formula (I)

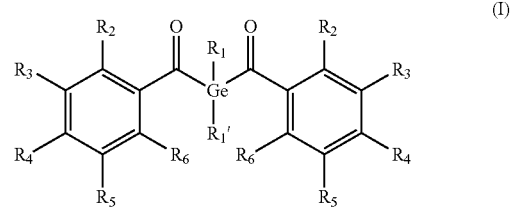

in which: $R_1$ and $R_1'$ are $C_1$ to $C_6$ alkyl; one or two of $R_2$, $R_3$, $R_4$, $R_5$, and $R_6$ are a hydrophilic group selected from the group consisting of $-CH_2(OCH_2CH_2)_{n1}-OCH_3$, $-CH_2(OCH_2CH_2)_{n1}-OH$,

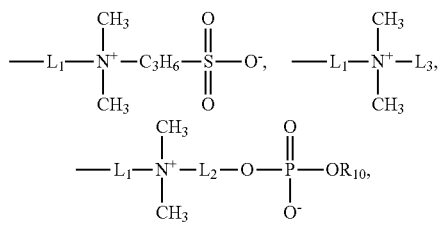

and $-L_1-SO_3H$ while the others of $R_2$, $R_3$, $R_4$, $R_5$, and $R_6$ independent of one another are hydrogen, methyl, or methoxy, wherein in which n1 is an integer of 2 to 20 (preferably 3 to 15, more preferably 4 to 10), $L_1$ is a direct bond or methylene diradical ($-CH_2-$), $L_2$ is ethylene diradical ($-C_2H_4-$) or propylene diradical ($-C_3H_6-$), $L_3$ is hydrogen or a $C_1$-$C_4$ alkyl, $R_{10}$ is methyl or ethyl.

In another aspect, the invention provides a method for producing UV-absorbing contact lenses, comprising the steps of: (1) obtaining an aqueous lens formulation, wherein the aqueous lens formulation comprises (a) at least one UV-absorbing vinylic monomer or a water-soluble UV-absorbing prepolymer (which comprises UV-absorbing moieties attached covalently thereonto) or a combination thereof, and (b) at least one acyl germanium photoinitiator of formula (I) as defined above; (2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) irradiating the aqueous lens formulation in the mold by using the light source including a light in a region of from 390 nm to 500 nm, so as to crosslink the lens-forming materials to form the UV-absorbing contact lens, wherein the formed UV-absorbing silicone hydrogel contact lens comprises an anterior surface defined by the first molding surface and an opposite posterior surface defined by the second molding surface and is characterized by having the UVB transmittance of about 10% or less between 280 and 315 nanometers and a UVA transmittance of about 30% or less between 315 and 380 nanometers and and optionally (but preferably) a Violet transmittance of about 60% or less between 380 nm and 440 nm.

The invention provides in a further aspect contact lenses obtained according to a method of the invention.

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

An "ophthalmic lens" refers to a contact lens and/or an intraocular lens. A "contact Lens" refers to a structure that can be placed on or within a wearer's eye. A contact lens can correct, improve, or alter a user's eyesight, but that need not be the case. A "silicone hydrogel contact lens" refers to a contact lens comprising a silicone hydrogel material.

As used in this application, the term "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

A "vinylic monomer" refers to a compound that has one sole ethylenically-unsaturated group.

The term "soluble", in reference to a compound or material in a solvent, means that the compound or material can be dissolved in the solvent to give a solution with a concentration of at least about 0.1% by weight at room temperature (i.e., a temperature of about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "olefinically unsaturated group" or "ethylenically unsaturated group" is employed herein in a broad sense and is intended to encompass any groups containing at least one >C=C< group. Exemplary ethylenically unsaturated groups include without limitation (meth)acryloyl

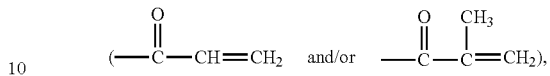

allyl, vinyl

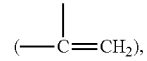

styrenyl, or other C=C containing groups.

The term "(meth)acrylamide" refers to methacrylamide and/or acrylamide.

The term "(meth)acrylamido" refers to an ethylenically-unsaturated group of

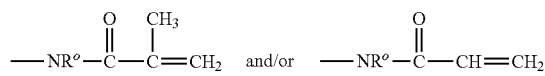

in which $R^0$ is hydrogen or $C_1$-$C_{10}$-alkyl.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

"UVA" refers to radiation occurring at wavelengths between 315 and 380 nanometers; "UVB" refers to radiation occurring between 280 and 315 nanometers; "Violet" refers to radiation occurring at wavelengths between 380 and 440 nanometers.

"UVA transmittance" (or "UVA % T"), "UVB transmittance" or "UVB % T", and "violet-transmittance" or "Violet % T" are calculated by the following formula $$UVA\ \%\ T = \frac{\text{Average \% Transmission between 315 and 380 nm}}{\text{Luminescence \% } T} \times 100$$

$$UVB\ \%\ T = \frac{\text{Average \% Transmission between 280 and 315 nm}}{\text{Luminescence \% } T} \times 100$$

$$Violet\ \%\ T = \frac{\text{Average \% Transmission between 380 and 440 nm}}{\text{Luminescence \% } T} \times 100$$

in which is Luminescence % T is determined by the following formula

Luminescence % T=Average % Transmission between 780-380 nm.

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "fluid" as used herein indicates that a material is capable of flowing like a liquid.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

A "photoinitiator" refers to a chemical that initiates free radical crosslinking/polymerizing reaction by the use of light.

A "UV-absorbing vinylic monomer" refers to a compound comprising an ethylenically-unsaturated group and a UV-absorbing moiety which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. A spatial limitation of UV radiation is obtained by using a mask or screen having a radiation (e.g., UV and/or visible light) permeable region, a radiation (e.g., UV and/or visible light) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation and/or visible radiation) having a cross-sectional profile defined by the projection contour of the mask or screen. The projected beam of radiation (e.g., UV radiation and/or visible radiation) limits radiation impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV and/or visible beam (i.e., a spatial limitation of radiation). The radiation used for the crosslinking is radiation energy, especially UV radiation (and/or visible radiation), gamma radiation, electron radiation or thermal radiation, the radiation energy preferably being in the form of a substantially parallel beam in order on the one hand to achieve good restriction and on the other hand efficient use of the energy.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

In general, the invention is directed to a class of acyl germanium photoinitiators which have increased solubility in water due to the presence of hydrophilic groups, can be activated with a visible light having a wavelength of from 390 nm to 500 nm to initiate a free radical polymerization reaction, and to the uses of such photoinitiators in making UV-absorbing contact lenses, in particularly, according to the Lightstream Technology™.

In one aspect, the present invention provides an acyl germanium photoinitiator of formula (I)

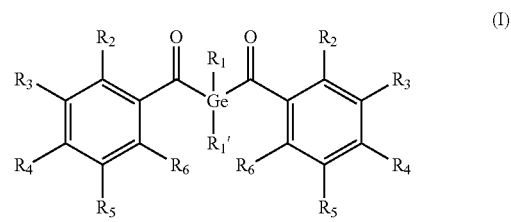

in which:

R$_1$ and R$_1$' are C$_1$ to C$_6$ alkyl, preferably C$_1$ to C$_4$ alkyl, more preferably methyl or ethyl;

one or two of R$_2$, R$_3$, R$_4$, R$_5$, and R$_6$ are a hydrophilic group selected from the group consisting of —CH$_2$(OCH$_2$CH$_2$)$_{n1}$—OCH$_3$, —CH$_2$(OCH$_2$CH$_2$)$_{n1}$—OH, -L$_1$-SO$_3$H,

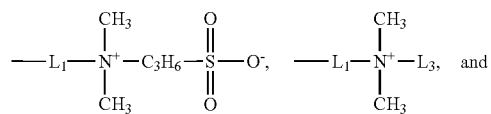

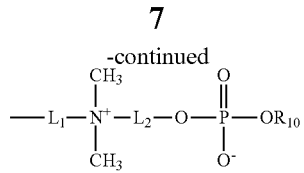

while the others of $R_2$, $R_3$, $R_4$, $R_5$, and $R_6$ independent of one another are hydrogen, methyl, or methoxy, wherein in which $n1$ is an integer of 2 to 20 (preferably 3 to 15, more preferably 4 to 10), $L_1$ is a direct bond or methylene diradical (—$CH_2$—), $L_2$ is ethylene diradical (—$C_2H_4$—) or propylene diradical (—$C_3H_6$—), $L_3$ is hydrogen or a $C_1$-$C_4$ alkyl (preferably methyl or ethyl), $R_{10}$ is methyl or ethyl.

Examples of preferred acyl germanium photoinitiators of formula (I) include without limitation:

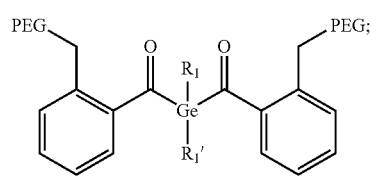 (I-1)

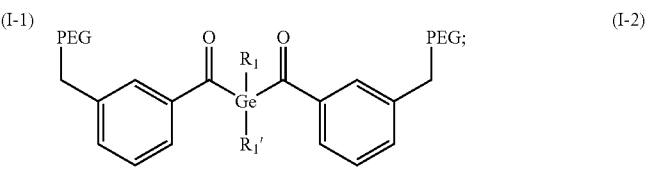 (I-2)

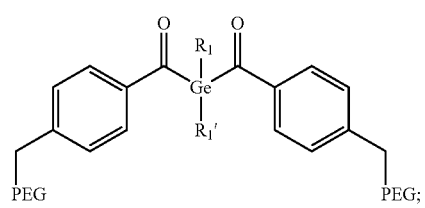 (I-3)

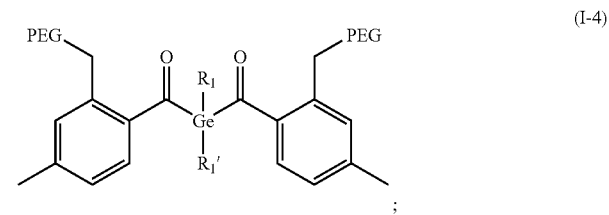 (I-4)

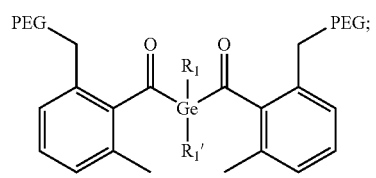 (I-5)

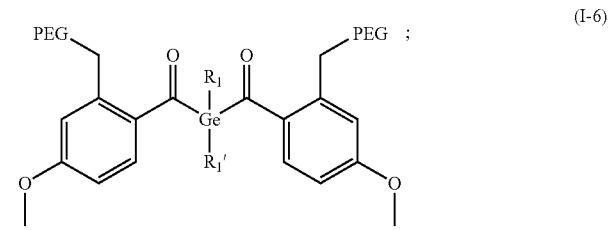 (I-6)

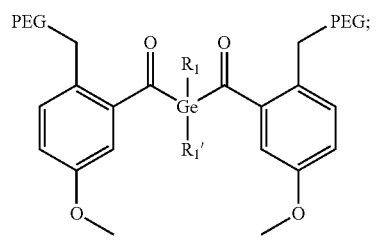 (I-7)

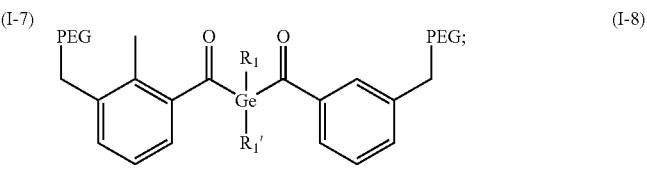 (I-8)

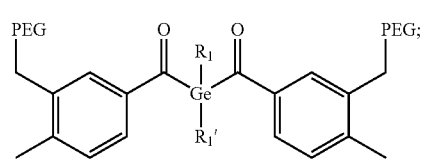 (I-9)

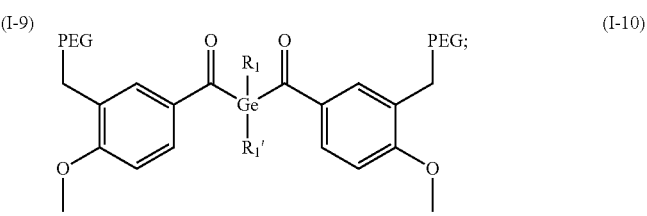 (I-10)

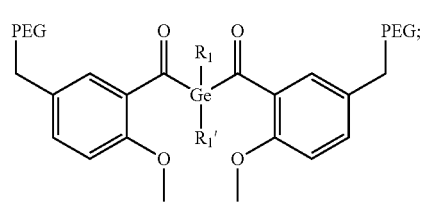 (I-11)

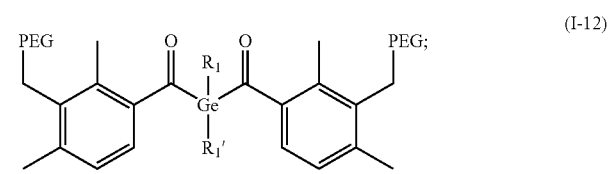 (I-12)

-continued
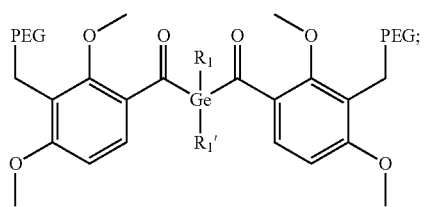
(I-13)
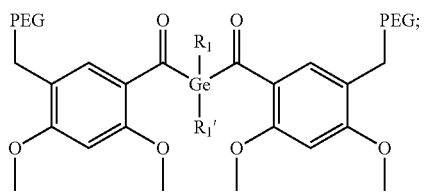
(I-14)
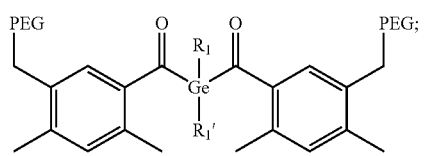
(I-15)
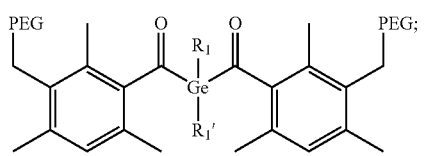
(I-16)
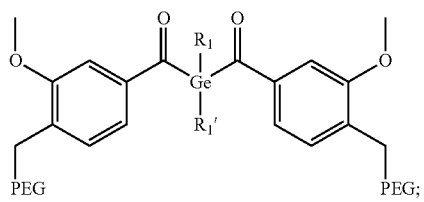
(I-17)
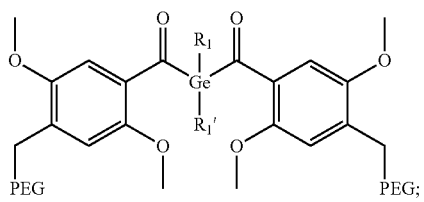
(I-18)
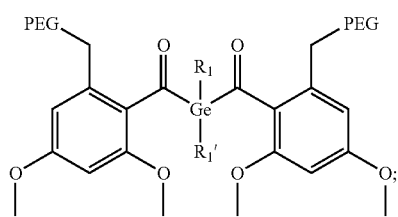
(I-19)
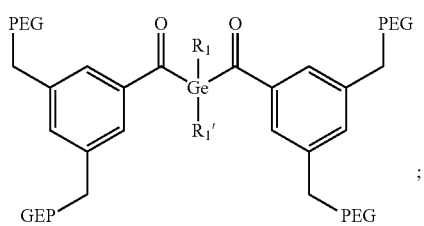
(I-20)
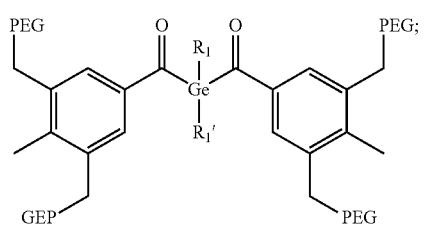
(I-21)
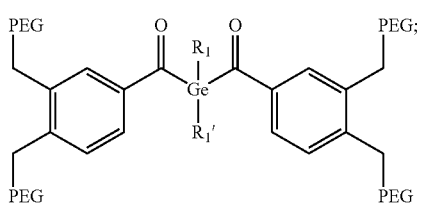
(I-22)
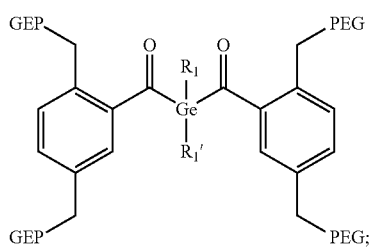
(I-23)
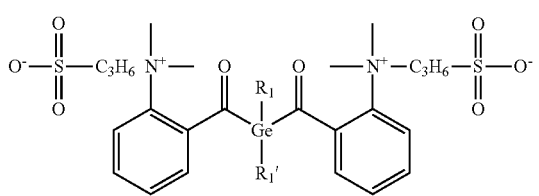
(I-24)
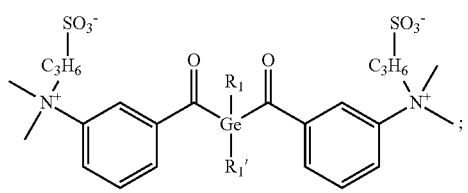
(I-25)
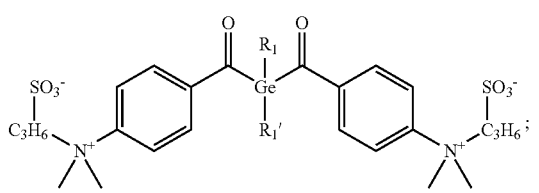
(I-26)

-continued
(I-27)
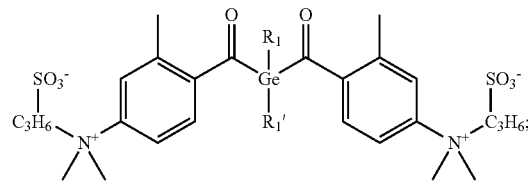
(I-28)
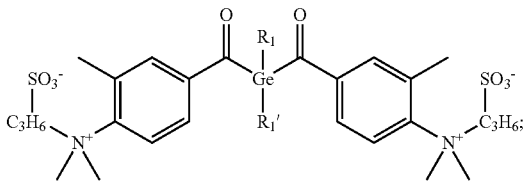
(I-29)
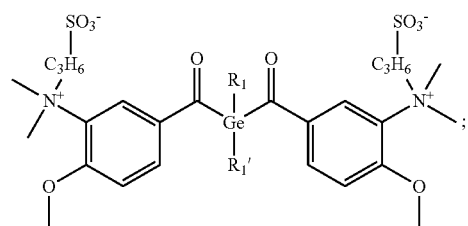
(I-30)
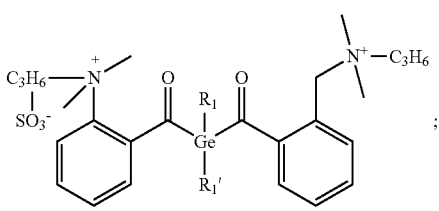
(I-31)
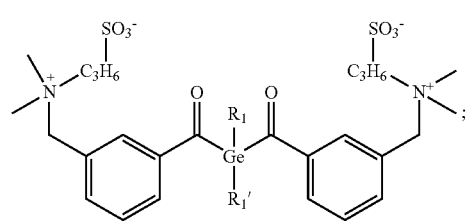
(I-32)
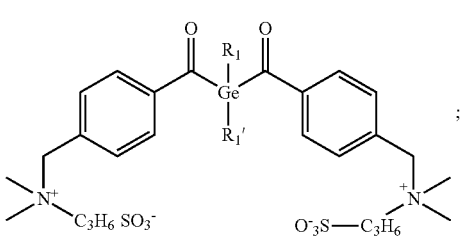
(I-33)
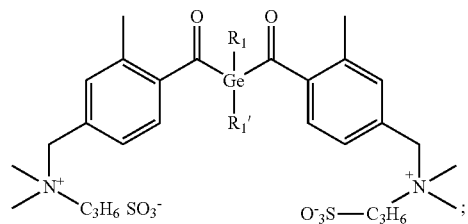
(I-34)
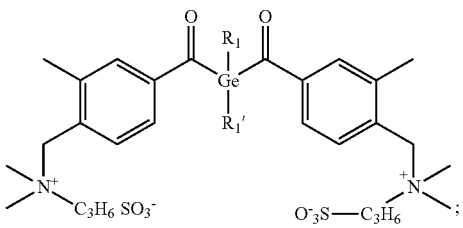
(I-35)
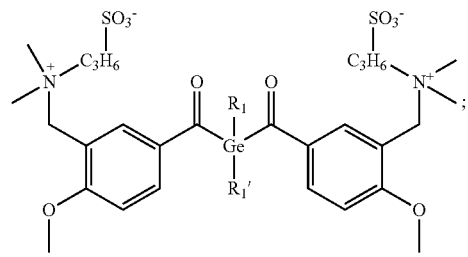
(I-36)
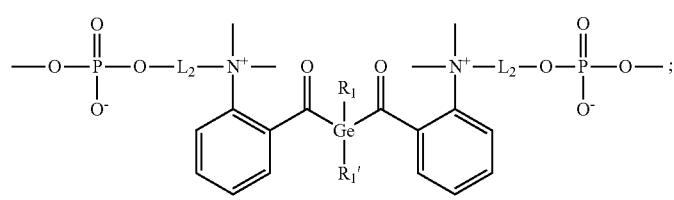
(I-37)
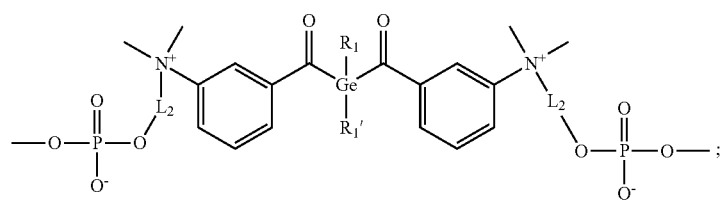

-continued
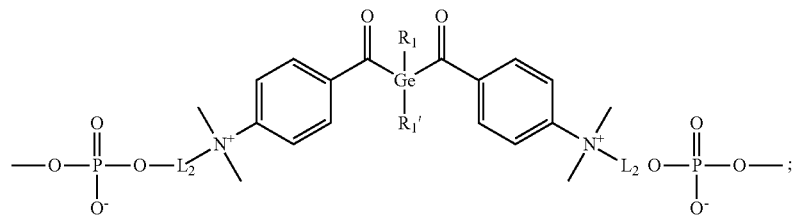
(I-38)
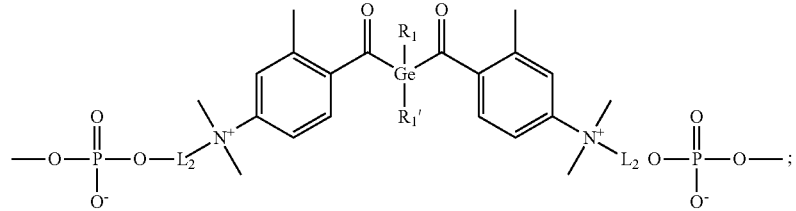
(I-39)
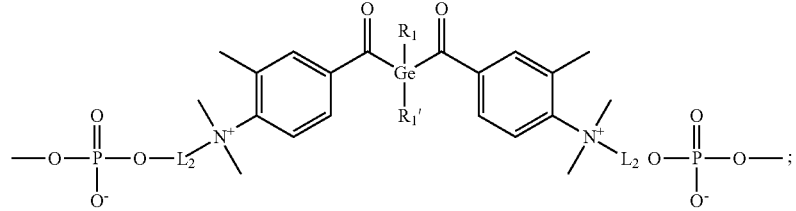
(I-40)
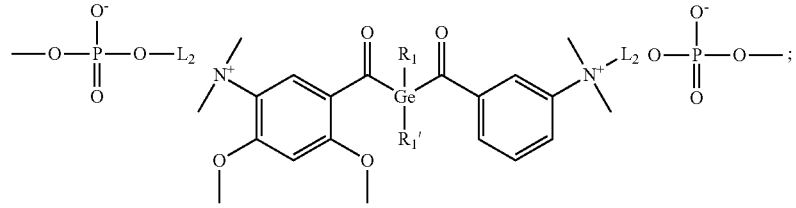
(I-41)
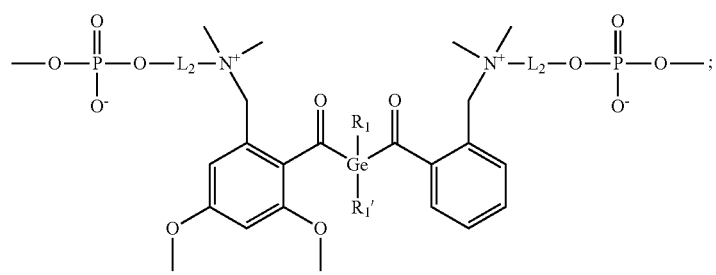
(I-42)
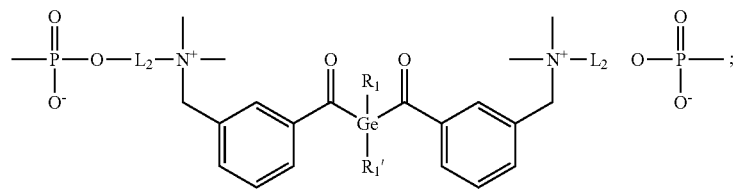
(I-43)
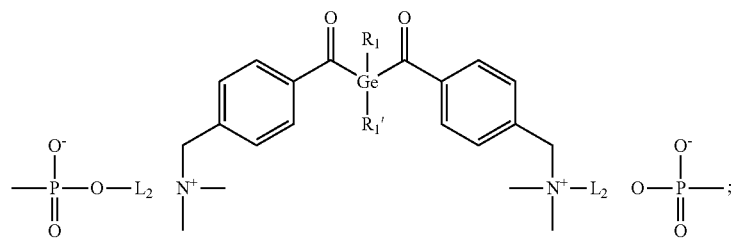
(I-44)

-continued
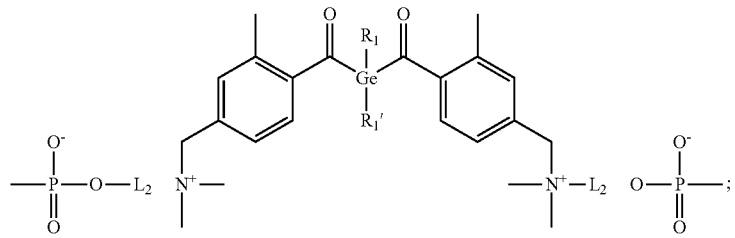
(I-45)
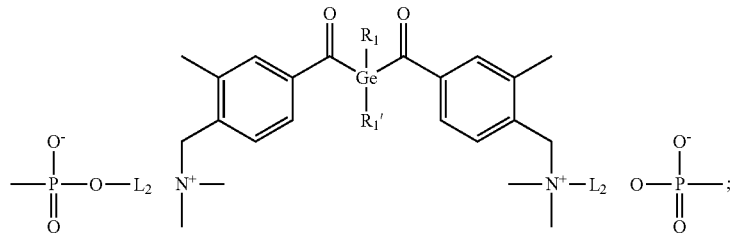
(I-46)
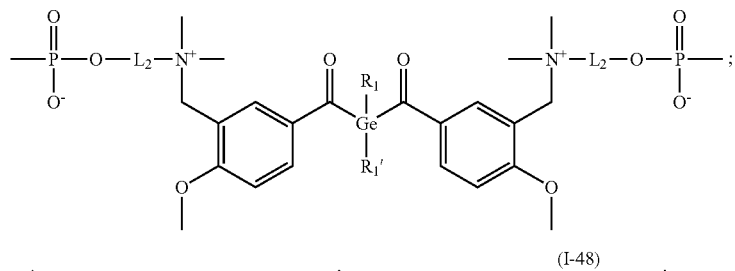
(I-47)
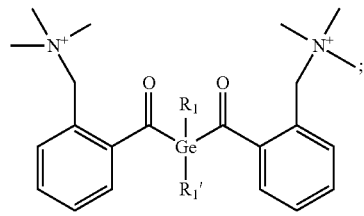
(I-48)
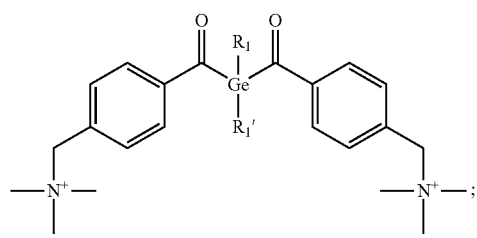
(I-49)
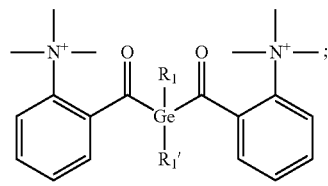
(I-50)
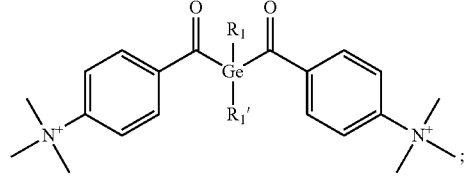
(I-52)
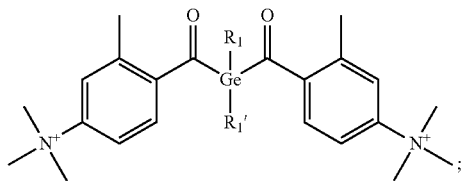
(I-53)

-continued

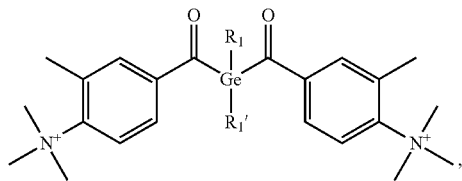 (I-56)

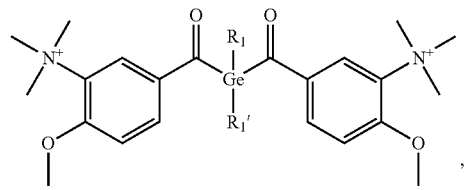 (I-57)

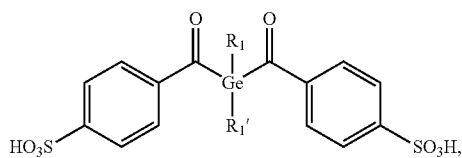 (I-58)

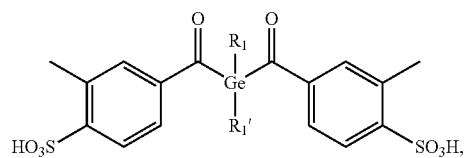 (I-59)

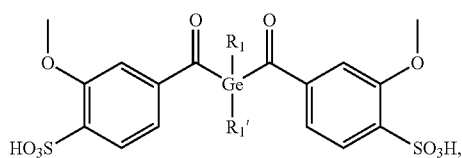 (I-60)

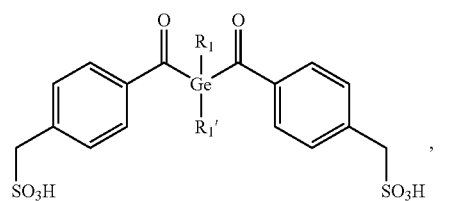 (I-61)

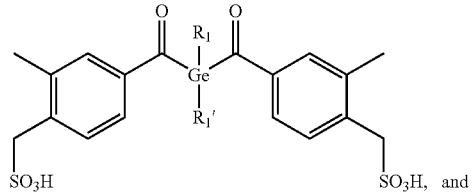 (I-62)

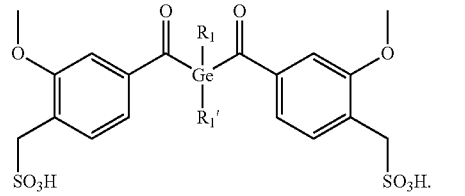 (I-63)

in which $R_1$ and $R_1'$ are $C_1$ to $C_6$ alkyl (preferably $C_1$ to $C_4$ alkyl, more preferably methyl or ethyl), PEG is a monovalent radical of —CH$_2$(OCH$_2$CH$_2$)$_{n1}$—OCH$_3$ or —CH$_2$(OCH$_2$CH$_2$)$_{n1}$—OH in which n1 is an integer of 2 to 20 (preferably 3 to 15, more preferably 4 to 10).

An acyl germanium photoinitiator of formula (I) defined above can be prepared from commercially-available starting materials, for example including but not limited to: (1) mono-(chloromethyl)-substituted benzoic acids (e.g., 2-(chloromethyl)benzoic acid, 3-(chloromethyl)benzoic acid, 4-(chloromethyl)benzoic acid, 2-(chloromethyl)-4-methylbenzoic acid, 2-(chloromethyl)-6-methylbenzoic acid, 2-(chloromethyl)-4-methoxybenzoic acid, 2-(chloromethyl)-5-methoxybenzoic acid, 2-(chloromethyl)-6-methoxybenzoic acid, 3-(chloromethyl)-2-methylbenzoic acid, 3-(chloromethyl)-4-methylbenzoic acid, 3-(chloromethyl)-4-methoxybenzoic acid, 5-(chloromethyl)-2-methoxybenzoic acid, 3-(chloromethyl)-2,4-dimethylbenzoic acid, 3-(chloromethyl)-2,4-dimethoxybenzoic acid, 3-(chloromethyl)-2,6-dimethoxybenzoic acid, 3-(chloromethyl)-2,6-dimethylbenzoic acid, 3-(chloromethyl)-2,4,6-trimethylbenzoic acid, 4-(chloromethyl)-3-methoxybenzoic acid, 4-(chloromethyl)-2,5-dimethoxybenzoic acid, 2-(chloromethyl)-4,6-dimethoxybenzoic acid); (2) mono-(bromomethyl)-substituted benzoic acids (e.g., 2-(bromomethyl)benzoic acid, 3-(bromomethyl)benzoic acid, 4-(bromomethyl)benzoic acid, 2-(bromomethyl)-4-methylbenzoic acid, 2-(bromomethyl)-6-methylbenzoic acid, 2-(bromomethyl)-4-methoxybenzoic acid, 2-(bromomethyl)-5-methoxybenzoic acid, 2-(bromomethyl)-6-methoxybenzoic acid, 3-(bromomethyl)-2-methylbenzoic acid, 3-(bromomethyl)-4-methyl benzoic acid, 3-(bromomethyl)-4-methoxybenzoic acid, 5-(bromomethyl)-2-methoxybenzoic acid, 3-(bromomethyl)-2,4-dimethylbenzoic acid, 3-(bromomethyl)-2,4-dimethoxybenzoic acid, 3-(bromomethyl)-2,6-dimethoxybenzoic acid, 3-(bromomethyl)-2,6-dimethylbenzoic acid, 3-(bromomethyl)-2,4,6-trimethylbenzoic acid, 4-(bromomethyl)-3-methoxybenzoic acid, 4-(bromomethyl)-2,5-dimethoxybenzoic acid, 2-(bromomethyl)-4,6-dimethoxybenzoic acid); (3) bis-(chloromethyl)-substituted benzoic acids or bis-(bromomethyl)-substituted benzoic acids (e.g., 3,5-bis(chloromethyl)benzoic acid, 3,5-bis(chloromethyl)-4-methylbenzoic acid, 3,4-bis(chloromethyl)benzoic acid, 2,5-bis(chloromethyl)benzoic acid, 3,5-bis(bromomethyl)benzoic acid, 3,5-bis(bromomethyl)-4-methylbenzoic acid, 3,4-bis(bromomethyl)benzoic acid, 2,5-bis(bromomethyl)benzoic acid); (4) mono-(dimethylamino)-substituted benzoic acids (e.g., 2-(dimethylamino)benzoic acid, 3-(dimethylamino)benzoic acid, 4-(dimethylamino)benzoic acid, 4-(dimethylamino)-2-methylbenzoic acid, 4-(dimethylamino)-3-methylbenzoic acid, 3-(dimethylamino)-4-methoxybenzoic acid); (5) mono-(dimethylaminomethyl)-substituted benzoic acids (e.g., 2-(dimethylaminomethyl)benzoic acid, 3-(dimethylaminomethyl)benzoic acid, 4-(dimethylaminomethyl)benzoic acid, 4-(dimethylaminomethyl)-2-methylbenzoic acid, 4-(dimethylaminomethyl)-3-methylbenzoic acid, 3-(dimethylaminomethyl)-4-methoxybenzoic acid); (6) dialkylgermanium dihydrides (e.g., dimethylgermanium dihydride, diethylgermanium dihydride, dipropylgermanium dihydride, dibutylgermanium dihydride, dipentylgermanium dihydride, dhexylgermanium dihydride); (7) 1,3-propanesultone; (8) alkyl alkylene phosphates (e.g., methyl ethylene phosphates, ethyl ethylene phosphates, methyl propylene phosphates, ethyl propylene phosphates); and (9) poly(ethyleneglycol) monomethyl ethers with various weight average molecular weights.

An acyl germanium photoinitiator of formula (I) defined above can be prepared from the above-listed starting materials or the likes according to various schemes, for example, such as, the following illustrative methods or the likes.

An acyl germanium photoinitiator of any one of formula (I-1) to (I-23) can be prepared by reacting a poly(ethylene glycol) monomethyl ether with a mono-(chloromethyl)-substituted benzoic acid, a mono-(bromomethyl)-substituted benzoic acid, a bis-(chloromethyl)-substituted benzoic acid, or a bis-(bromomethyl)-substituted benzoic acid, to substitute the chlorine or bromine atom with a monovalent radical of —CH$_2$(OCH$_2$CH$_2$)$_{n1}$—OCH$_3$ or —CH$_2$(OCH$_2$CH$_2$)$_{n1}$—OH in which n1 is an integer of 2 to 20 (preferably 3 to 15, more preferably 4 to 10); converting the resultant carboxylic acid group into an acyl chloride according to a known reaction, e.g., by using oxalyl chloride; reacting the resultant acy chloride with a dialkylgermanium dilithium which can be obtained from the reaction of a dialkylgermanium dihydride with tert-butyl lithium, to obtain a photoinitiator of the invention, under conditions known to a person skilled in the art (see, for example, Castel, A; Piviere, P.; Satge, J.; Ko, H. Y. *Organometallics* 1990, 9, 205, herein incorporated by reference in its entirety), as illustrated in Scheme I.

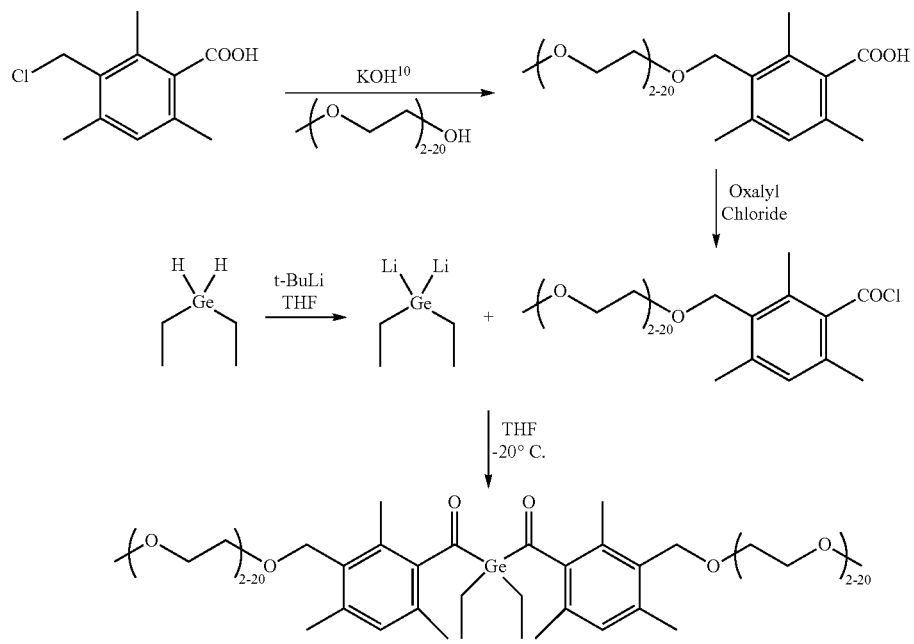

Scheme I

An acyl germanium photoinitiator of any one of formula (I-24) to (I-35) can be prepared by reacting a dialkylgermanium dilithium with a (dimethylamino)-substituted or (dimethylaminomethyl)-substituted benzoic acid, to a dibenzoyldimethylgermanium compound; reacting the resultant dibenzoyldimethylgermanium compound with 1,3-propane sultone, under conditions known to a person skilled in the art (see, for example, Lascelles, S. F.; Malet, F.; Mayada, R.; Billingham, N. C.; Armes, S. P. *Macromolecules* 1999, 32(8), 2462, herein incorporated by reference in its entirety), as illustrated in Scheme II, to obtain a photoinitiator of the invention.

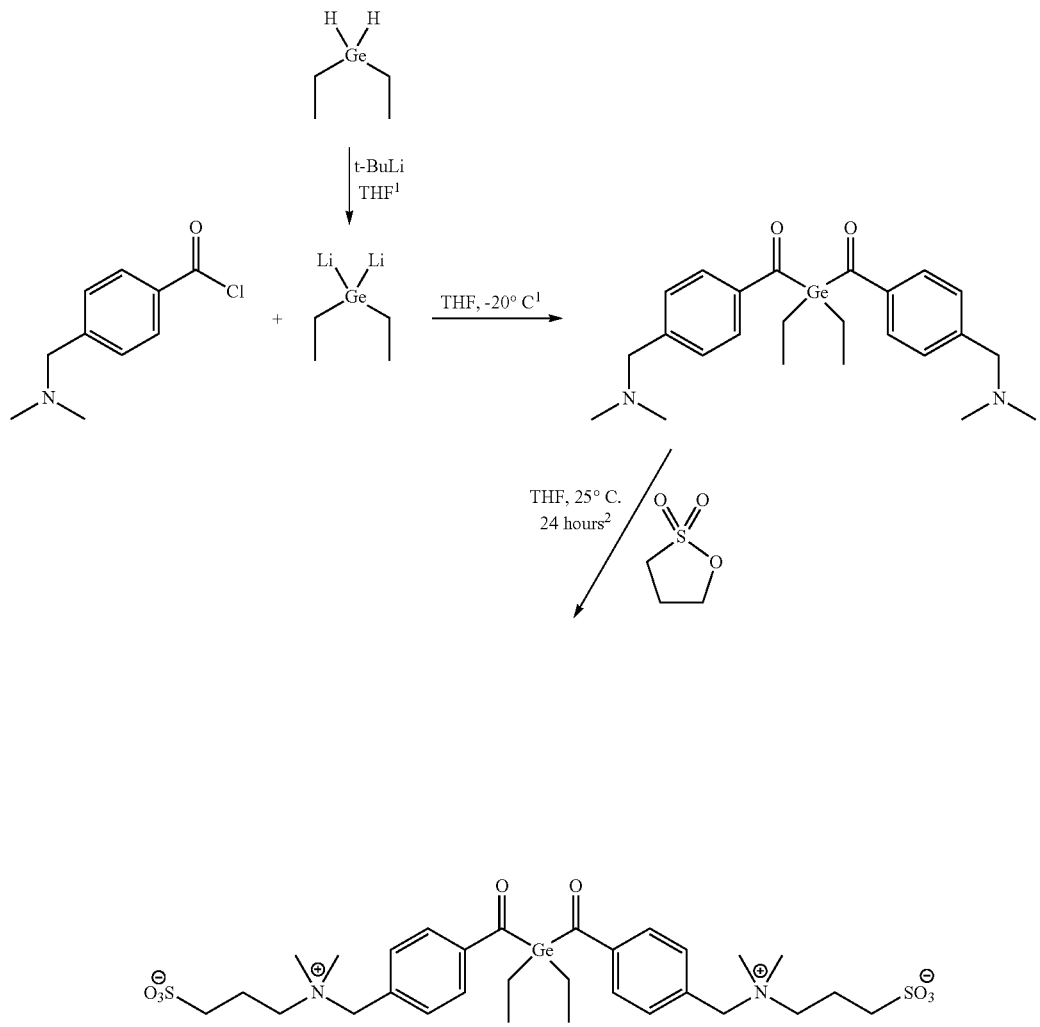

Scheme II

An acyl germanium photoinitiator of any one of formula (I-36) to (I-47) can be prepared by reacting a dialkylgermanium dilithium with a (dimethylamino)-substituted or (dimethylaminomethyl)-substituted benzoic acid, to a dibenzoyldimethylgermanium compound; reacting the resultant dibenzoyldimethylgermanium compound with alkyl alkylene phosphate (e.g., methyl ethylene phosphate, ethyl ethylene phosphate, methyl propylene phosphate, or ethyl propylene phosphate), under conditions known to a person skilled in the art, as illustrated in Scheme III, to obtain a photoinitiator of the invention (Makromol. Chem., Rapid Commun. 3, 457-459 (1982).

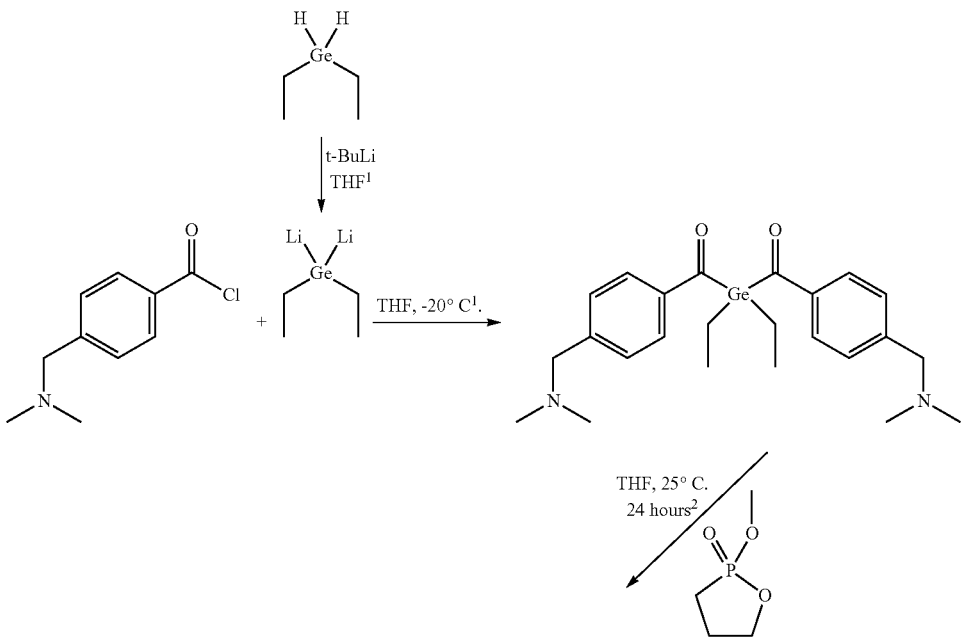

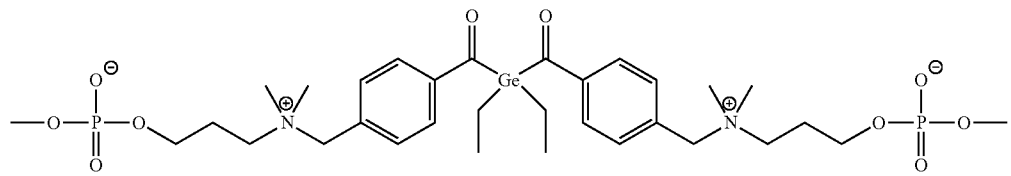

An acyl germanium photoinitiator of any one of formula (I-48) to (I-57) can be prepared by reacting a dialkylgermanium dilithium with a (dimethylamino)-substituted or (dimethylaminomethyl)-substituted benzoic acid, to a dibenzoyldiethylgermanium compound; reacting the resultant dibenzoyldiethylgermanium compound with methyl bromide or other agents known to form the quaternary salts under conditions known to a person skilled in the art, as illustrated in Scheme IV, to obtain a photoinitiator of the invention. Other counterions can be used instead of bromide. (Journal of Bioactive and Compatible Polymer, 5, 1990, 31 and ThermochimicaActa, 134, (1988), 49-54)

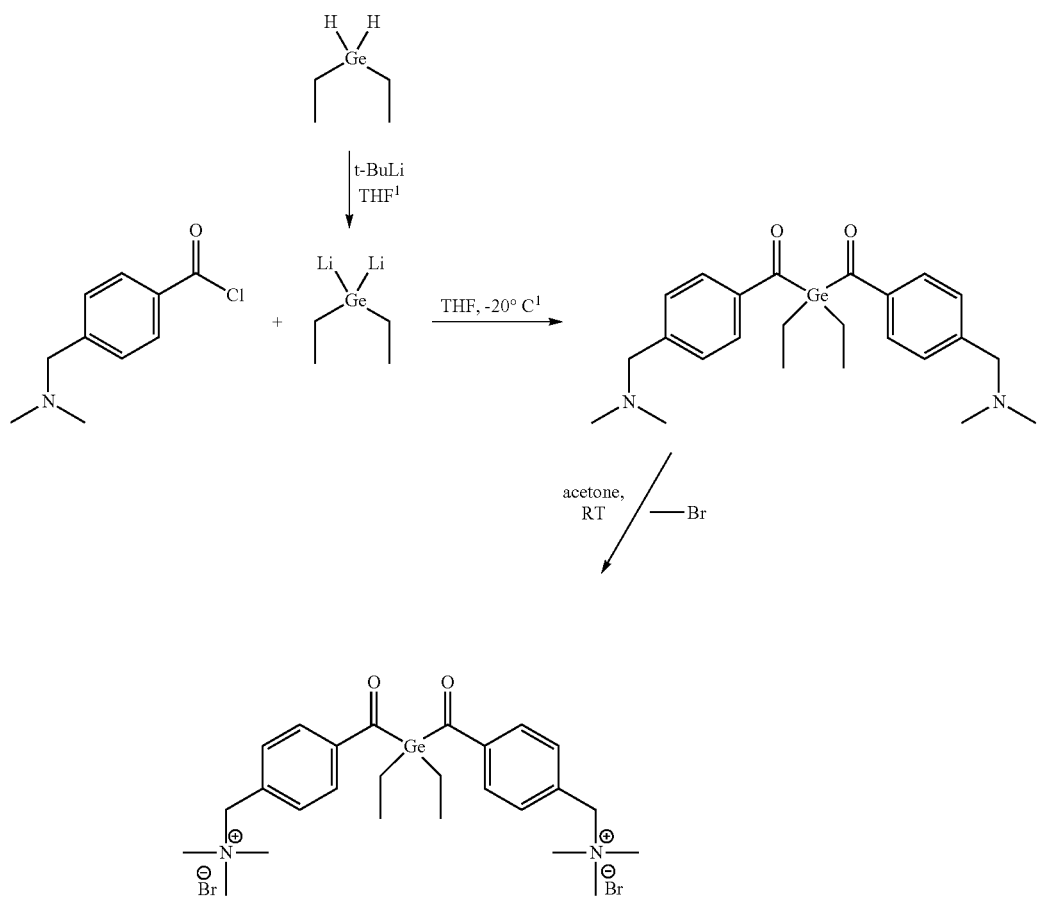

An acyl germanium photoinitiator of any one of formula (I-58) to (I-63) can be prepared by reacting a dialkylgermanium dilithium with a (dithioester)-substituted or (dithioestermethyl)-substituted benzoic acid, to a dibenzoyldiethylgermanium compound; deprotecting the thioester, then oxidizing to the resultant dibenzoyldiethylgermanium compound. Other reagents and conditions can be used by known by persons skilled in the art as illustrated in Scheme V. (*JACS* 1963, 85, 1337; *J. Med. Chem* 1985, 28, 328; *Tetrahedron Letters* 2008, 49, 3291)

Scheme V

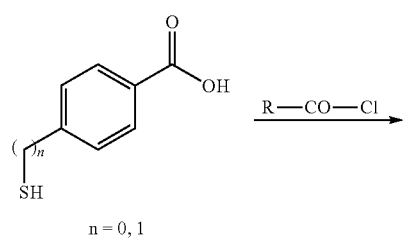

n = 0, 1

-continued

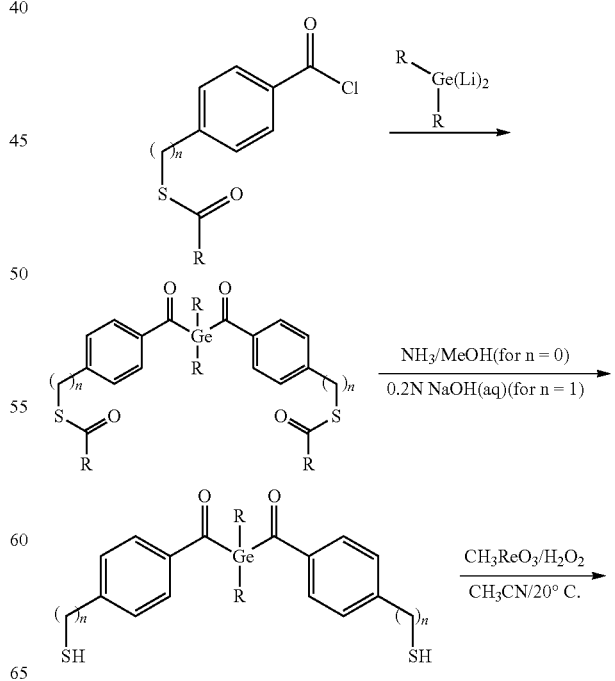

-continued

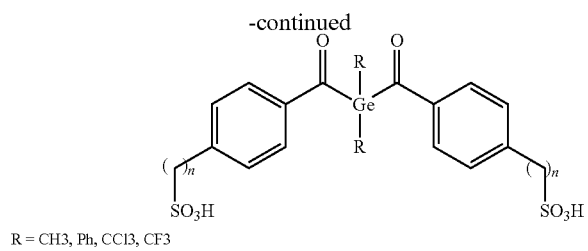

R = CH3, Ph, CCl3, CF3

An acyl germanium photoinitiator of formula (I) as defined above can find use in making UV-absorbing contact lenses, in particularly, according to the Lightstream Technology™, which is another aspect of the invention.

In another aspect, the invention provides a method for producing UV-absorbing contact lenses, comprising the steps of: (1) obtaining an aqueous lens formulation, wherein the aqueous lens formulation comprises (a) at least one UV-absorbing vinylic monomer or a water-soluble UV-absorbing prepolymer (which comprises UV-absorbing moieties attached covalently thereonto) or a combination thereof, and (b) from about 0.1% to about 2.0% by weight of, preferably from about 0.25% to about 1.75% by weight of, more preferably from about 0.5% to about 1.5% by weight of, even more preferably from about 0.75% to about 1.25% by weight of at least one acyl germanium photoinitiator of formula (I) as defined above; (2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) irradiating the aqueous lens formulation in the mold by using the light source including a light in a region of from 390 nm to 500 nm, so as to crosslink the lens-forming materials to form the UV-absorbing contact lens, wherein the formed UV-absorbing silicone hydrogel contact lens comprises an anterior surface defined by the first molding surface and an opposite posterior surface defined by the second molding surface and is characterized by having the UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and and optionally (but preferably) a Violet transmittance of about 60% or less, preferably about 50% or less, more preferably about 40% or less, even more preferably about 30% or less) between 380 nm and 440 nm.

An "aqueous lens formulation" refers to a polymerizable composition which comprises water as solvent or a solvent mixture comprising at least about 60% (preferably at least about 80%, more preferably at least about 90%, even more preferably at least about 95%, most preferably at least about 98%) by weight of water relative to the total amount of the solvent mixture and polymerizable/crosslinkable components, and which can be cured (i.e., polymerized and/or crosslinked) thermally or actinically to obtain a crosslinked/polymerized polymeric material. Polymerizable components for making contact lenses are well known to a person skilled in the art, including, for example, such as, monomers, macromers, prepolymers, or combinations thereof, as known to a person skilled in the art. A lens formulation can further include other components, such as an initiator (e.g., a photoinitiator or a thermal initiator), a visibility tinting agent, UV-absorbing vinylic monomers, photoinitiators, photosensitizers, antimicrobial agents (e.g., Ag-nanoparticles), lubricant/wetting agents, and the like.

A preferred group of prepolymers are those which are soluble in water or a water-organic solvent mixture and and are ophthalmically compatible. It would be advantageous that an actinically-crosslinkable prepolymer are in a substantially pure form (e.g., purified by ultrafiltration to remove most reactants for forming the prepolymer). Therefore, after crosslinking by actinic radiation, a contact lens may require practically no more subsequent purification, such as in particular complicated extraction of unpolymerized constituents. Furthermore, crosslinking may take place in aqueous solution, so that a subsequent solvent exchange or the hydration step is not necessary.

Examples of preferred actinically crosslinkable prepolymers include, but are not limited to, a water-soluble actinically-crosslinkable poly(vinyl alcohol) prepolymer described in U.S. Pat. Nos. 5,583,163 and 6,303,687 (incorporated by reference in their entireties); a water-soluble vinyl group-terminated polyurethane prepolymer described in U.S. Patent Application Publication No. 2004/0082680 (herein incorporated by reference in its entirety); a water-soluble prepolymer disclosed in U.S. Pat. No. 5,849,841 (incorporated by reference in its entirety); a water-soluble actinically-crosslinkable polyurea prepolymer described in U.S. Pat. No. 6,479,587 and in commonly owned pending U.S. patent application Ser. No. 10/991,124 filed on Nov. 17, 2004 (herein incorporated by reference in their entireties); a water-soluble actinically-crosslinkable polyacrylamide; a water-soluble actinically-crosslinkable statistical copolymer of vinyl lactam, MMA and a comonomer, which are disclosed in EP 655,470 and U.S. Pat. No. 5,712,356 (herein incorporated by references in their entireties); a water-soluble actinically-crosslinkable copolymer of vinyl lactam, vinyl acetate and vinyl alcohol, which are disclosed in EP 712,867 and U.S. Pat. No. 5,665,840 (herein incorporated by references in their entireties); a water-soluble polyether-polyester copolymer with actinically-crosslinkable side chains which are disclosed in EP 932,635 and U.S. Pat. No. 6,492,478 (herein incorporated by references in their entireties); a water-soluble branched polyalkylene glycol-urethane prepolymer disclosed in EP 958,315 and U.S. Pat. No. 6,165,408 (herein incorporated by references in their entireties); a water-soluble polyalkylene glycol-tetra(meth)acrylate prepolymer disclosed in EP 961,941 and U.S. Pat. No. 6,221,303 (herein incorporated by references in their entireties); and a water-soluble actinically-crosslinkable polyallylamine gluconolactone prepolymer disclosed in PCT patent application WO 2000/31150 and U.S. Pat. No. 6,472,489 (herein incorporated by references in their entireties). Preferred concentrations of the prepolymer in solution are from approximately 15 to approximately 50% by weight, especially from approximately 15 to approximately 40% by weight, for example from approximately 25% to approximately 40% by weight.

Preferably, the prepolymers used in the process according to the invention are previously purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the concentration of dissolved salts obtained as by-products, which can be determined simply in known manner.

In a preferred embodiment, an actinically-crosslinkable prepolymer is a water-soluble crosslinkable poly(vinyl alcohol).

In another preferred embodiment, an actinically-crosslinkable prepolymer is a crosslinkable polyurea as described in U.S. Pat. No. 6,479,587 or in a commonly assigned copending U.S. patent application Ser. No. 10/991,124 filed on Nov. 17, 2004 (herein incorporated by reference in their entireties).

Any suitable UV-absorbing vinylic monomers, or polymer with UV absorbing capability, can be used in the invention. A UV-absorbing vinylic monomer used in the invention comprises a benzophenone-moiety, preferably a benzotriazole-moiety. In a preferred embodiment, a UV-absorbing vinylic monomer, or polymer with UV absorbing capability, used in the invention is a benzotriazole-containing UV/HEVL absorber that absorbs both ultraviolet light and high-energy violet light (HEVL) and preferably is represented by formula

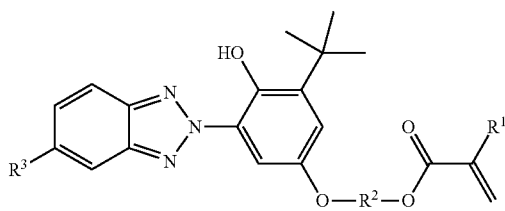

wherein $R^1$=H or $CH_3$; $R^2$=$C_2$-$C_{10}$ alkylene divalent group or preferably $C_2$-$C_4$ alkylene divalent group; and $R^3$=H, $CH_3$, $CH_3O$, F, Cl, Br, I, or $CF_3$. Preparation of those UV/HEVL absorbers of the above formula are described in U.S. Pat. Nos. 8,153,703 and 8,232,326, which are herein incorporated by references in their entireties. Benzotriazole-containing UV-absorbing vinyl monomers can be prepared according to procedures described in U.S. Pat. Nos. 3,299,173, 4,612,358, 4,716,234, 4,528,311 (herein incorporated by reference in their entireties) or can be obtained from commercial suppliers.

Examples of preferred benzophenone-containing UV-absorbing vinylic monomers include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof. Benzophenone-containing UV-absorbing vinyl monomers can be prepared according to procedures described in U.S. Pat. No. 3,162,676 (herein incorporated by reference in its entirety) or can be obtained from commercial suppliers.

Examples of preferred UV-absorbing and UV/HEVL-absorbing, benzotriazole-containing vinylic monomers include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5-methacryloxyethylphenyl) benzotriazole (2-Propenoic acid, 2-methyl-, 2-[3-(2H-benzotriazol-2-yl)-4-hydroxyphenyl] ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$—UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-[2'-Hydroxy-3'-tert-butyl-5'-(3'-methacryloyloxypropoxy)phenyl]-5-trifluoromethyl-2H-benzotriazole ($CF_3$—UV23), 2-[2'-Hydroxy-3'-tert-butyl-5'-(3'-methacryloyloxypropoxy)phenyl]-5-chloro-2H-benzotriazole (UV28), 2-[2'-Hydroxy-3'-tert-butyl-5'-(3'-acryloyloxypropoxy)phenyl]-5-chloro-2H-benzotriazole, 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (901) (CAS#83063-87-0).

Examples of more preferred UV-absorbing vinylic monomers include 2-[2'-Hydroxy-3'-tert-butyl-5'-(3'-methacryloyloxypropoxy)phenyl]-5-trifluoromethyl-2H-benzotriazole ($CF_3$—UV23), 2-[2'-Hydroxy-3'-tert-butyl-5'-(3'- methacryloyloxypropoxy)phenyl]-5-chloro-2H-benzotriazole (UV28), 2-[2'-Hydroxy-3'-tert-butyl-5'-(3'-acryloyloxypropoxy)phenyl]-5-chloro-2H-benzotriazole, 2-[2'-Hydroxy-3'-tert-butyl-5'-(3'-acryloyloxypropoxy)phenyl]-5-trifluoromethyl-2H-benzotriazole ($CF_3$—UV13), 2-[3-(2H-benzotriazol-2-yl)-4-hydroxyphenyl]ethyl ester (Norbloc), 2-{2'-Hydroxy-3'-tert-butyl-5'-[3'-methacryloyloxypropoxy]phenyl}-5-methoxy-2H-benzotriazole (UV13), or a mixture thereof.

In a more preferred embodiment, UV-absorbing moieties, such as, benzophenone-moieties or benzotriazole-moieties or combinations thereof are covalently attached to a water-soluble, actinically-crosslinkable prepolymer, for example, such as, actinically-crosslinkable PVA, to make a water-soluble UV-absorbing prepolymer.

It is understood that the amount of at least one UV-absorbing vinylic monomer, or a water-soluble UV-absorbing polymer, in the aqueous lens formulation is sufficient to render a contact lens, which is obtained from the curing of the lens formulation, ability of blocking or absorbing (i.e., the inverse of transmittance) at least 90% (preferably at least about 95%, more preferably at least about 97.5%, even more preferably at least about 99%) of UVB (between 280 and 315 nanometers), at least 70% (preferably at least about 80%, more preferably at least about 90%, even more preferably at least about 95%) of UVA transmittance (between 315 and 380 nanometers), and optionally (but preferably) at least 30% (preferably at least about 40%, more preferably at least about 50%, even more preferably at least about 60%) of violet light between 380 nm and 440 nm, which impinge on the lens.

In accordance with the present invention, the aqueous lens formulation can also comprise a hydrophilic vinylic monomer. Nearly any hydrophilic vinylic monomer can be used in the invention. Suitable hydrophilic vinylic monomers are, without this being an exhaustive list, N,N-dimethylacrylamide (DMA), N,N-dimethylmethacrylamide (DMMA), 2-acrylamidoglycolic acid, N-hydroxypropylacrylamide, N-hydroxyethyl acrylamide, N-[tris(hydroxymethyl)methyl]-acrylamide, N-vinylpyrrolidone, N-vinyl formamide, N-vinyl acetamide, N-vinyl isopropylamide, N-vinyl-N-methyl acetamide, N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), a $C_1$-$C_4$-alkoxy polyethylene glycol (meth)acrylate having a weight average molecular weight of up to 1500, polyethylene glycol (meth)acrylate having a weight average molecular weight of up to 1500, methacrylic acid, acrylic acid, and mixtures thereof.

An aqueous lens formulation of the invention can also comprise a non-silicone hydrophobic monomer (i.e., free of silicone). By incorporating a certain amount of non-silicone hydrophobic vinylic monomer in a lens formulation, the mechanical properties (e.g., modulus of elasticity) of the resultant polymer may be improved. Nearly any non-silicone hydrophobic vinylic monomer can be used in the actinically polymerizable composition for preparing the intermediary copolymer with pendant or terminal functional groups. Examples of preferred non-silicone hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

In a preferred embodiment, the aqueous lens formulation may further comprise a crosslinking agent, preferably selected from the group consisting of N,N'-methylene-bis-(meth)acrylamide, N,N'-ethylene-bis-(meth)acrylamide, N,N'-dihydroxyethylene-bis-(meth)acrylamide, 1,3-bis(methacrylamidopropyl)-1,1,3,3-tetramethyldisiloxane, ethylene glycol di(meth)acrylate, diethylene glycol di(meth)acrylate, triethylene glycol di(meth)acrylate, tetraethylene glycol di(meth)acrylate, glycerol di(meth)acrylate, triallyl isocyanurate, triallyl cyanurate, N-allyl-(meth)acrylamide, tetraethyleneglycol divinyl ether, triethyleneglycol divinyl ether, diethyleneglycol divinyl ether, ethyleneglycol divinyl ether, and combinations thereof.

An aqueous lens formulation of the invention can further comprise visibility tinting agents (e.g., D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, or mixtures thereof), antimicrobial agents (e.g., silver nanoparticles), a bioactive agent (e.g., a drug, an amino acid, a polypeptide, a protein, a nucleic acid, 2-pyrrolidone-5-carboxylic acid (PCA), an alpha hydroxyl acid, linoleic and gamma linoleic acids, vitamins, or any combination thereof), leachable lubricants (e.g., a non-crosslinkable hydrophilic polymer having an average molecular weight from 5,000 to 500,000, preferably from 10,000 to 300,000, more preferably from 20,000 to 100,000 Daltons), leachable tear-stabilizing agents (e.g., a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof), and the like, as known to a person skilled in the art.

An aqueous lens formulation can be prepared by dissolving all of the desirable components in water or a mixture of water and an organic solvent known to a person skilled in the art.

Lens molds for making contact lenses are well known to a person skilled in the art. Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference. Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

Preferably, a reusable mold suitable for spatial limitation of radiation is used in the invention, the projected beam of radiation (e.g., radiation from the light source including the light in the region of 360 nm to 550 nm) limits radiation (e.g., UV radiation) impinging on the mixture of the lens-forming materials located in the path of the projected beam from the first molding surface to the second molding surface of the reusable mold. The resultant contact lens comprises an anterior surface defined by the first molding surface, an opposite posterior surface defined by the second molding surface, and a lens edge (with sharp edge and high quality) defined by the sectional profile of the projected radiation beam (i.e., a spatial limitation of radiation). Examples of reusable molds suitable for spatial limitation of radiation include without limitation those disclosed in U.S. Pat. Nos. 6,627,124, 6,800,225, 7,384,590, and 7,387,759, which are incorporated by reference in their entireties.

For example, a preferred reusable mold comprises a first mold half having a first molding surface and a second mold half having a second molding surface. The two mold halves of the preferred reusable mold are not touching each other, but there is a thin gap of annular design arranged between the two mold halves. The gap is connected to the mold cavity formed between the first and second molding surfaces, so that excess mixture can flow into the gap. It is understood that gaps with any design can be used in the invention.

In a preferred embodiment, at least one of the first and second molding surfaces is permeable to a crosslinking radiation. More preferably, one of the first and second molding surfaces is permeable to a crosslinking radiation while the other molding surface is poorly permeable to the crosslinking radiation.

The reusable mold preferably comprises a mask which is fixed, constructed or arranged in, at or on the mold half having the radiation-permeable molding surface. The mask is impermeable or at least of poor permeability compared with the permeability of the radiation-permeable molding surface. The mask extends inwardly right up to the mold cavity and surrounds the mold cavity so as to screen all areas behind the mask with the exception of the mold cavity.

The mask may preferably be a thin chromium layer, which can be produced according to processes as known, for example, in photo and UV lithography. Other metals or metal oxides may also be suitable mask materials. The mask can also be coated with a protective layer, for example of silicon dioxide if the material used for the mold or mold half is quartz.

Alternatively, the mask can be a masking collar made of a material comprising a UV-absorber and substantially blocks curing energy therethrough as described in U.S. Pat. No. 7,387,759 (incorporated by reference in its entirety). In this preferred embodiment, the mold half with the mask comprises a generally circular disc-shaped transmissive portion and a masking collar having an inner diameter adapted to fit in close engagement with the transmissive portion, wherein said transmissive portion is made from an optically clear material and allows passage of curing energy therethrough, and wherein the masking collar is made from a material comprising a light-blocker and substantially blocks passage of curing energy therethrough, wherein the masking collar generally resembles a washer or a doughnut, with a center hole for receiving the transmissive portion, wherein the transmissive portion is pressed into the center opening of the masking collar and the masking collar is mounted within a bushing sleeve.

Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J. Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc. Because of the reusability of the mold halves, a relatively high outlay can be expended at the time of their production in order to obtain molds of extremely high precision and reproducibility. Since the mold halves do not touch each other in the region of the lens to be produced, i.e. the cavity or actual molding surfaces, damage as a result of contact is ruled out. This ensures a high service life of the molds, which, in particular, also ensures high reproducibility of the contact lenses to be produced and high fidelity to the lens design.

In accordance with the invention, the lens formulation can be introduced (dispensed) into a cavity formed by a mold according to any known methods.

After the lens formulation is dispensed into the mold, it is polymerized to produce a contact lens. Crosslinking may be initiated upon exposure to a light source including a light in a region between 390 nm to 500 nm, preferably under a spatial limitation of actinic radiation, to crosslink the polymerizable components in the mixture.

In accordance with the invention, light source can be any ones emitting light in the 390-500 nm range sufficient to activate Germane-based Norrish Type I photoinitiators. Blue-light sources are commercially available and include: the Palatray CU blue-light unit (available from Heraeus Kulzer, Inc., Irvine, Calif.), the Fusion F450 blue light system (available from TEAMCO, Richardson, Tex.), Dymax Blue Wave 200, LED light sources from Opsytec (385 nm, 395 nm, 405 nm, 435 nm, 445 nm, 460 nm), LED light sources from Hamamatsu (385 nm), and the GE 24" blue fluorescent lamp (available from General Electric Company, U.S.). A preferred blue-light source is the UV LED from Opsytec (those described above).

The intensity of the light source is preferably from about 4 to about 40 mW/cm$^2$, preferably from about 8 to about 16 mW/cm$^2$ in the 410 nm to 550 nm region is more preferred.

The crosslinking according to the invention may be effected in a very short time, e.g. in ≤about 120 seconds, preferably in ≤about 80 seconds, more preferably in ≤50 about seconds, even more preferably in ≤about 30 seconds, and most preferably in 5 to 30 seconds.

Opening of the mold so that the molded lens can be removed from the mold may take place in a manner known per se.

The molded contact lens can be subject to lens extraction to remove unpolymerized vinylic monomers and macromers. The extraction solvent is preferably water or an aqueous solution. After extraction, lenses can be hydrated in water or an aqueous solution of a wetting agent (e.g., a hydrophilic polymer); packaged in lens packages with a packaging solution which can contain about 0.005% to about 5% by weight of a wetting agent (e.g., a hydrophilic polymer), a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization such as autoclave at from 118 to 124° C. for at least about 30 minutes; and the like.

A contact lens of the invention preferably is characterized by having an average Violet-transmittance of about 60% or less (preferably about 50% or less, more preferably about 40% or less) between 380 and 440 nanometers.

A contact lens of the invention further has a water content of preferably from about 15% to about 80%, more preferably from about 30% to about 70% by weight (at room temperature, about 22° C. to 28° C.) when fully hydrated.

It should be understood that although in this aspect of the invention various embodiments including preferred embodiments of the invention may be separately described above, they can be combined and/or used together in any desirable fashion to arrive at different embodiments of a contact lenses of the invention.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. An acyl germanium photoinitiator of formula (I)

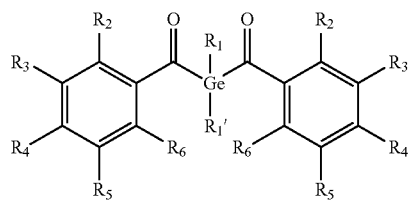

in which:

$R_1$ and $R_1'$ are $C_1$ to $C_6$ alkyl, preferably $C_1$ to $C_4$ alkyl; one or two of $R_2$, $R_3$, $R_4$, $R_5$, and $R_6$ are a hydrophilic group selected from the group consisting of —$CH_2(OCH_2CH_2)_{n1}$—$OCH_3$, —$CH_2(OCH_2CH_2)_{n1}$—OH, -$L_1$-$SO_3H$,

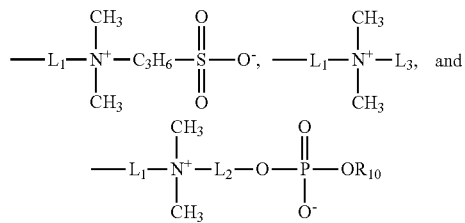

while the others of $R_2$, $R_3$, $R_4$, $R_5$, and $R_6$ independent of one another are hydrogen, methyl, or methoxy, wherein in which n1 is an integer of 2 to 20 (preferably 3 to 15, more preferably 4 to 10), $L_1$ is a direct bond or methylene diradical (—$CH_2$—), $L_2$ is ethylene diradical (—$C_2H_4$—) or propylene diradical (—$C_3H_6$—), $L_3$ is hydrogen or a $C_1$-$C_4$ alkyl, $R_{10}$ is methyl or ethyl.

2. The acyl germanium photoinitiator of invention 1, wherein $R_1$ and $R_1'$ are $C_1$ to $C_4$ alkyl.
3. The acyl germanium photoinitiator of invention 1, wherein $R_1$ and $R_1'$ are methyl or ethyl.
4. The acyl germanium photoinitiator of invention 1, 2 or 3, wherein n1 is an integer of 3 to 15.
5. The acyl germanium photoinitiator of invention 1, 2 or 3, wherein n1 is an integer of 4 to 10.
6. The acyl germanium photoinitiator of any one of inventions 1 to 5, wherein $L_3$ is methyl or ethyl.
7. The acyl germanium photoinitiator of any one of inventions 1 to 6, wherein only one of $R_2$, $R_3$, $R_4$, $R_5$, and $R_6$ is a hydrophilic group selected from the group consisting of

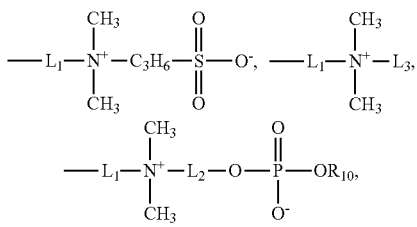

—$CH_2(OCH_2CH_2)_{n1}$—$OCH_3$, —$CH_2(OCH_2CH_2)_{n1}$—OH, and -L-$SO_3H$ while the others of $R_2$, $R_3$, $R_4$, $R_5$, and $R_6$ independent of one another are hydrogen, methyl, or methoxy.

8. The acyl germanium photoinitiator of any one of inventions 1 to 6, wherein two of $R_2$, $R_3$, $R_4$, $R_5$, and $R_6$ are a hydrophilic group selected from the group consisting of

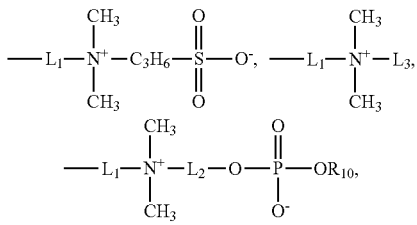

—$CH_2(OCH_2CH_2)_{n1}$—$OCH_3$, —$CH_2(OCH_2CH_2)_{n1}$—OH, and -$L_1$-$SO_3H$ while the others of $R_2$, $R_3$, $R_4$, $R_5$, and $R_6$ independent of one another are hydrogen, methyl, or methoxy.

9. The acyl germanium photoinitiator of any one of inventions 1 to 8, wherein the hydrophilic group is —$CH_2(OCH_2CH_2)_{n1}$—$OCH_3$ or —$CH_2(OCH_2CH_2)_{n1}$—OH.

10. The acyl germanium photoinitiator of any one of inventions 1 to 8, wherein the hydrophilic group is

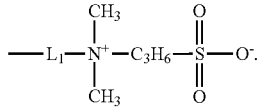

11. The acyl germanium photoinitiator of any one of inventions 1 to 8, wherein the hydrophilic group is

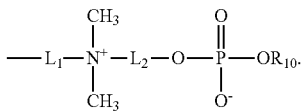

12. The acyl germanium photoinitiator of any one of inventions 1 to 8, wherein the hydrophilic group is

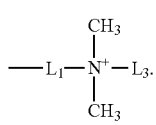
13. The acyl germanium photoinitiator of any one of inventions 1 to 8, wherein the hydrophilic group is -$L_1$-$SO_3H$ in which $L_1$ is a direct bond or methylene diradical (—$CH_2$—).
14. The acyl germanium photoinitiator of any one of inventions 1 to 6, having a formula selected from the group consisting of formula (I-1) to (I-63):
(I-1)
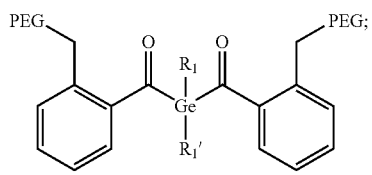
(I-2)
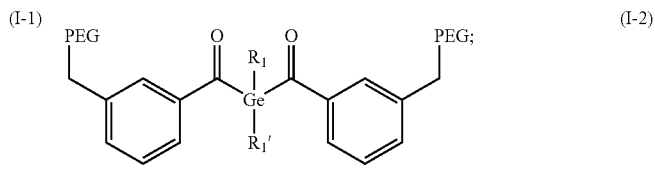
(I-3)
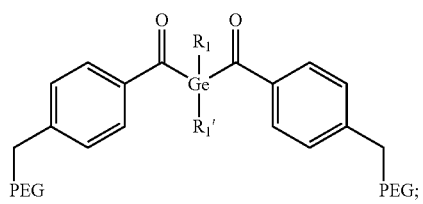
(I-4)
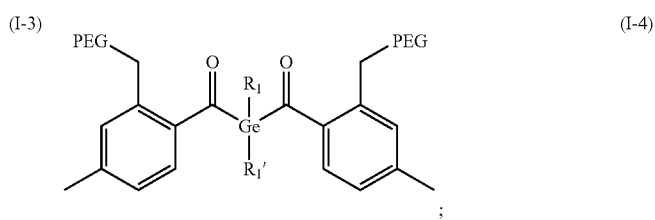
(I-5)
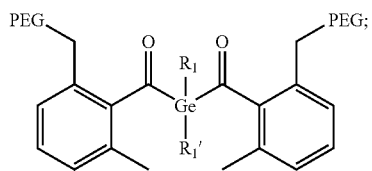
(I-6)
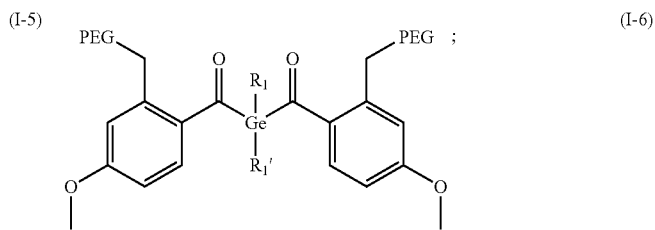
(I-7)
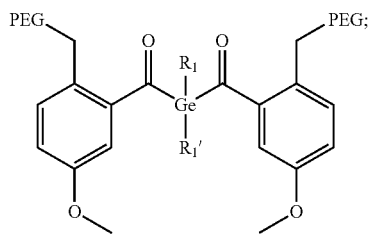
(I-8)
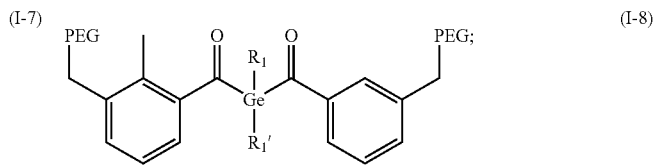
(I-9)
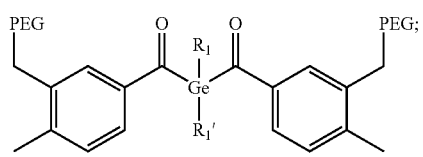
(I-10)
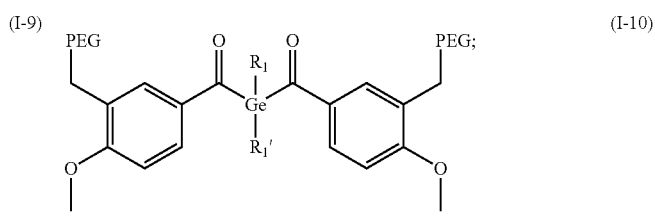
(I-11)
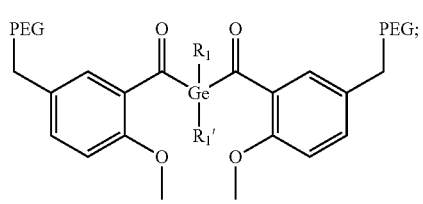
(I-12)
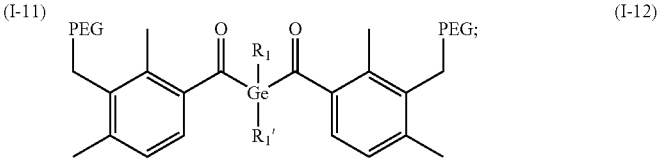

-continued
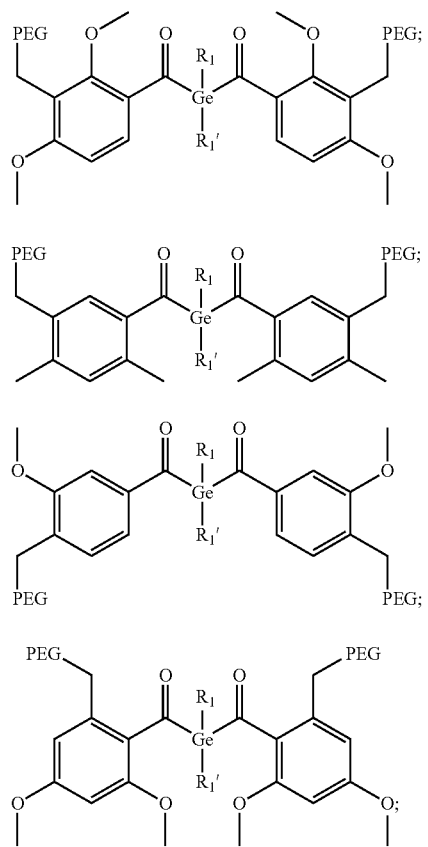
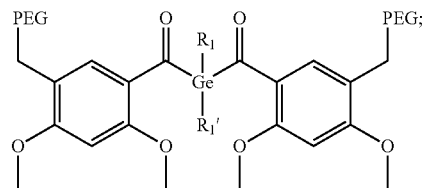
(I-13) (I-14)
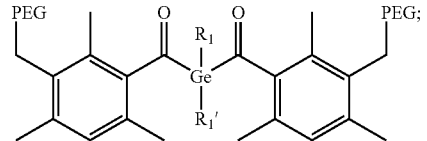
(I-15) (I-16)
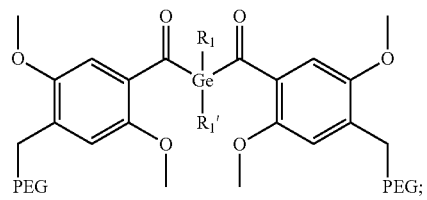
(I-17) (I-18)
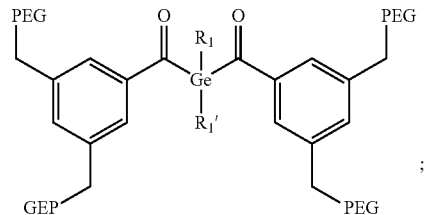
(I-19) (I-20)
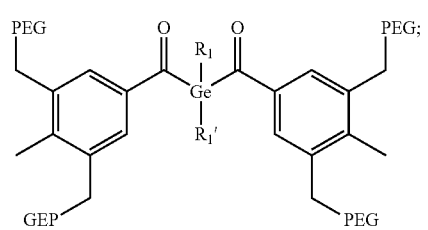
(I-21)
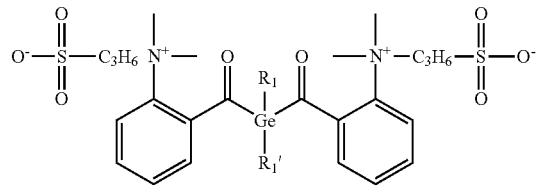
(I-22) (I-24)
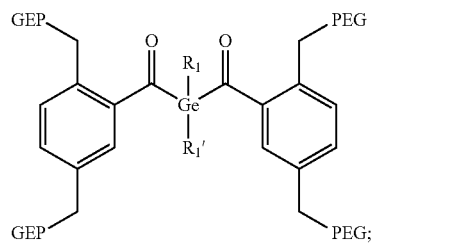
(I-23)
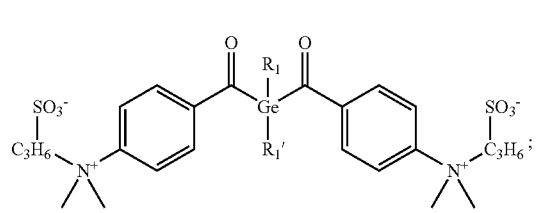
(I-25) (I-26)

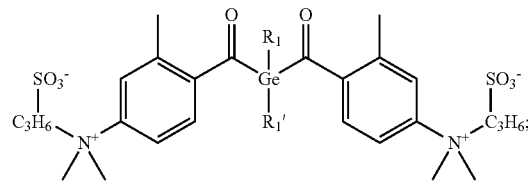
(I-27)
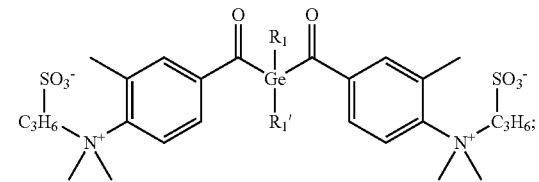
(I-28)
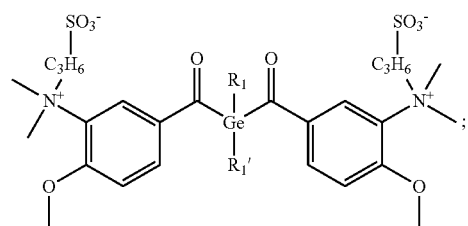
(I-29)
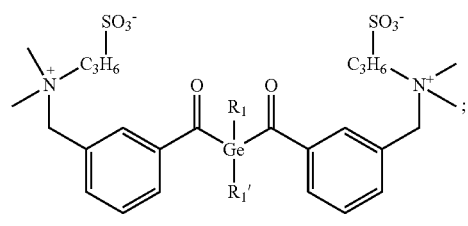
(I-30)
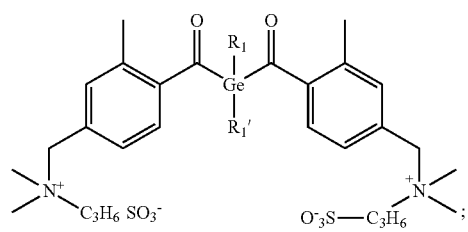
(I-31)
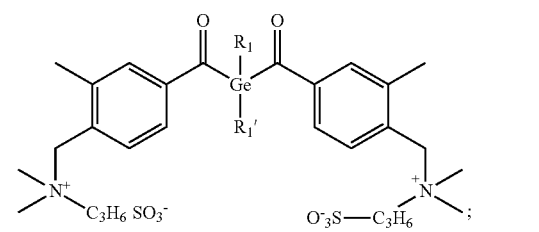
(I-32)
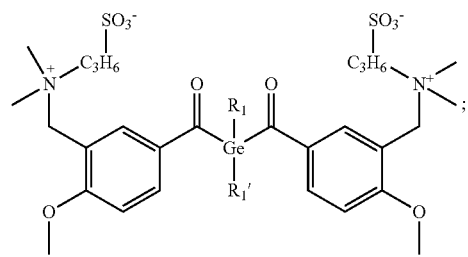
(I-33)
(I-34)
(I-35)
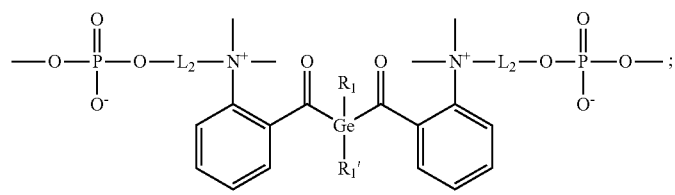
(I-36)
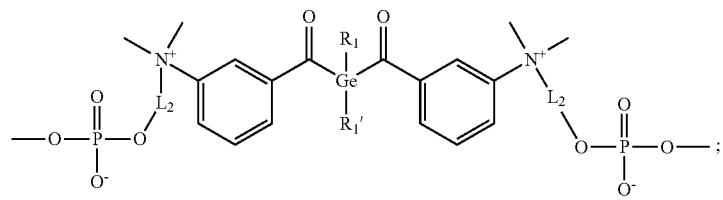
(I-37)

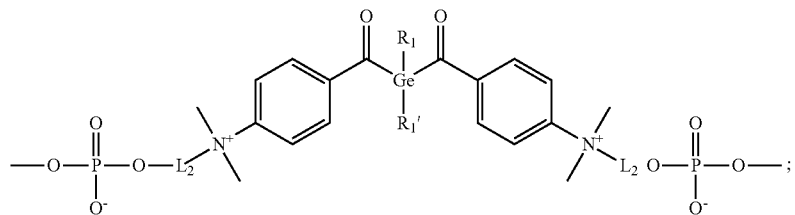
(I-38)
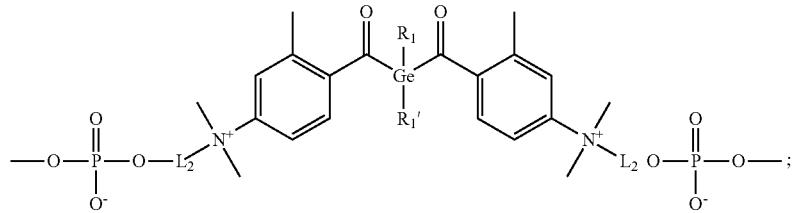
(I-39)
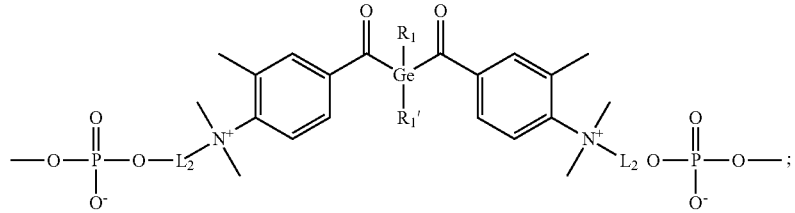
(I-40)
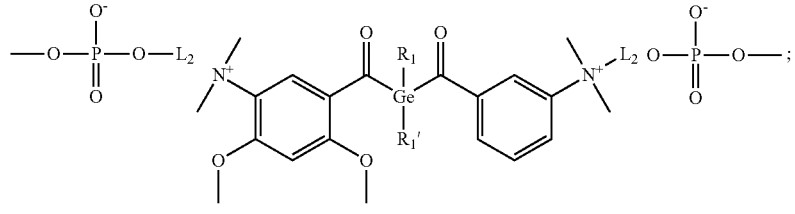
(I-41)
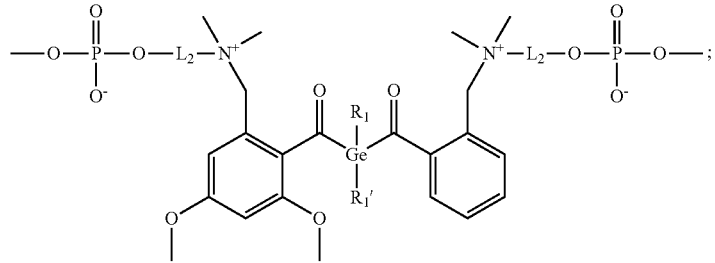
(I-42)
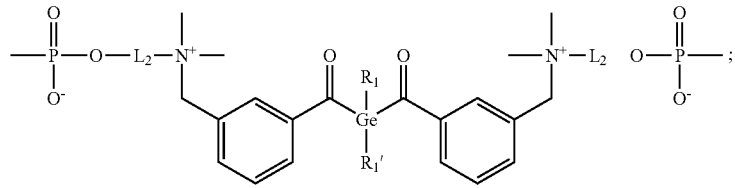
(I-43)
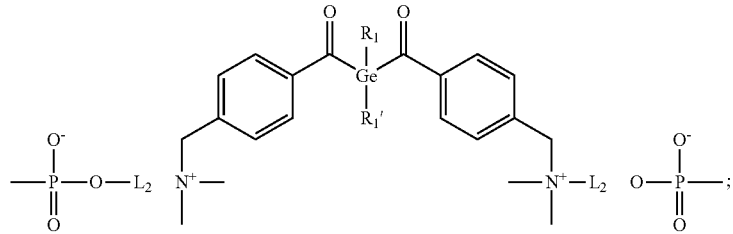
(I-44)

(I-45)
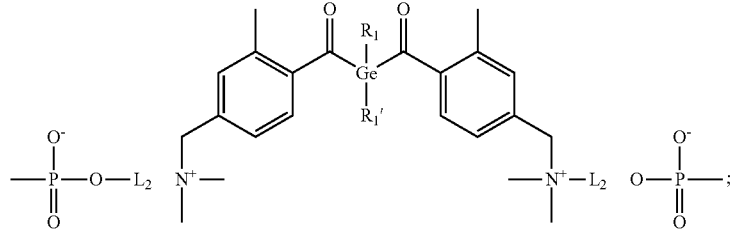
(I-46)
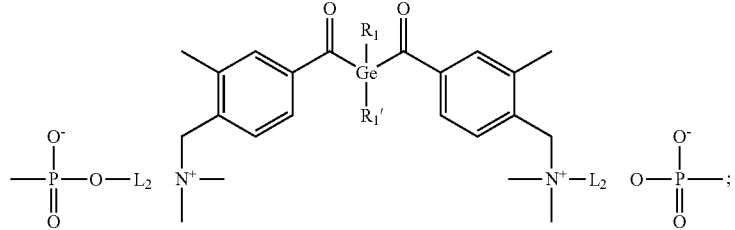
(I-47)
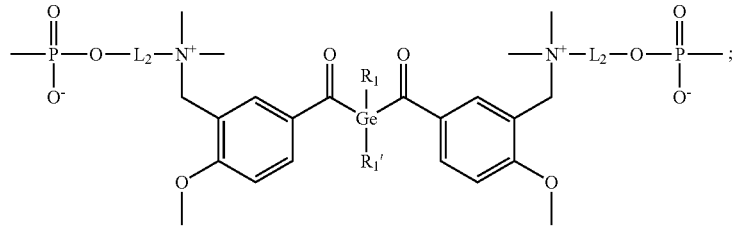
(I-48)
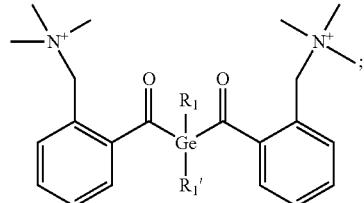
(I-49)
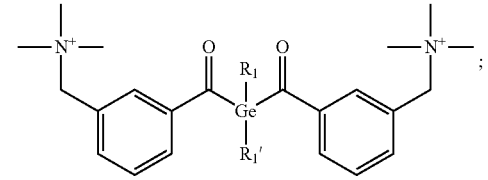
(I-50)
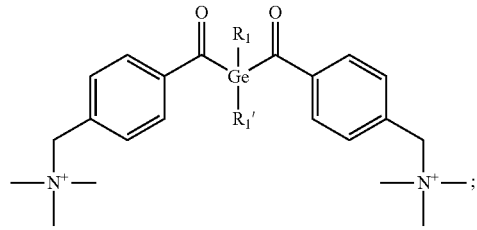
(I-51)
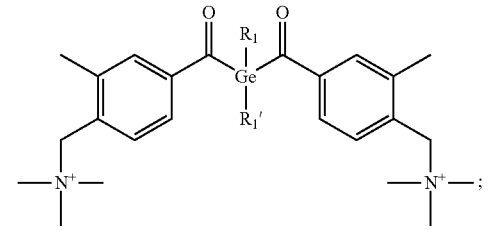
(I-52)
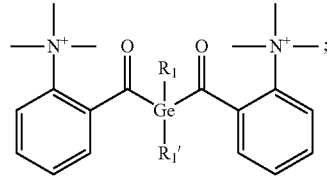
(I-53)
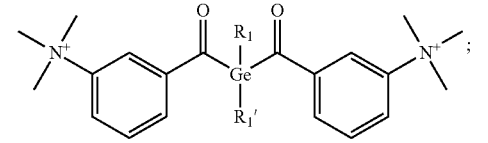
(I-54)
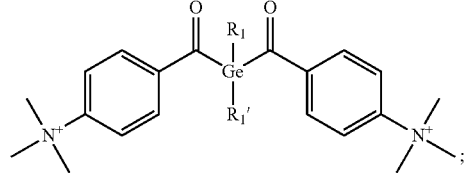
(I-55)
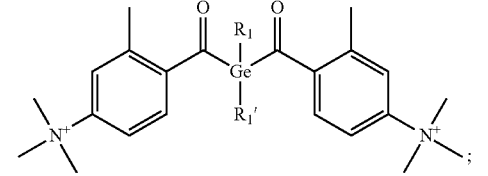

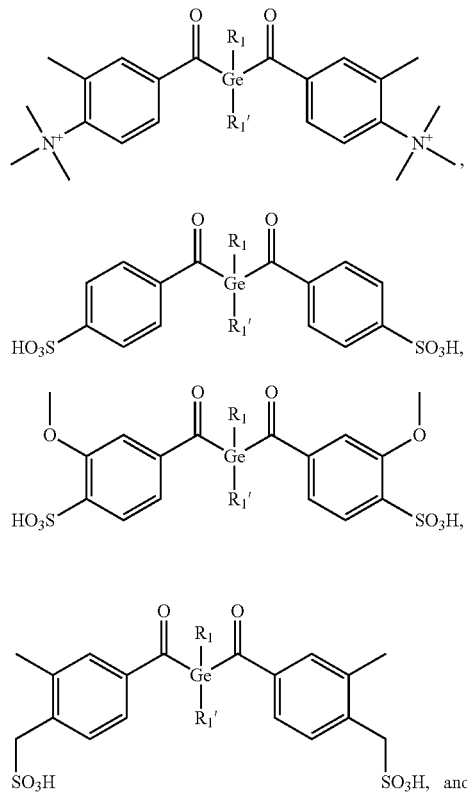

in which PEG is a monovalent radical of —CH$_2$(OCH$_2$CH$_2$)$_{n1}$—OCH$_3$ or —CH$_2$(OCH$_2$CH$_2$)$_{n1}$—OH in which n1 is an integer of 2 to 20 (preferably 3 to 15, more preferably 4 to 10).

15. A method for producing UV-absorbing silicone hydrogel contact lenses, the method comprising the steps of:
(1) obtaining an aqueous lens formulation, wherein the aqueous lens formulation comprises
 (a) from about 0.1% to about 2.0% by weight of at least one acyl germanium photoinitiator of any one of inventions 1 to 14, and
 (b) at least one UV-absorbing vinylic monomer, or a water-soluble UV-absorbing prepolymer (which comprises UV-absorbing moieties attached covalently thereto), and
(2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and
(3) irradiating the aqueous lens formulation in the mold by using a light source including a light in a region of from 390 nm to 500 nm, so as to crosslink the lens-forming materials to form the UV-absorbing contact lens, wherein the formed UV-absorbing silicone hydrogel contact lens comprises an anterior surface defined by the first molding surface and an opposite posterior surface defined by the second molding surface and is characterized by having a UVB transmittance of about 10% or less between 280 and 315 nanometers and a UVA transmittance of about 30% or less between 315 and 380 nanometers.

16. The method according to invention 15, wherein the aqueous lens formulation comprises from about 0.25% to about 1.75% by weight of (preferably from about 0.5% to about 1.5% by weight of, more preferably from about 0.75% to about 1.25% by weight of) at least one acyl germanium photoinitiator of any one of inventions 1 to 14

17. The method according to invention 15 or 16, wherein the formed UV-absorbing silicone hydrogel contact lens is characterized by having the UVB transmittance of about 5% or less (preferably about 2.5% or less, even more preferably about 1% or less) between 280 and 315 nanometers.

18. The method according to any one of inventions 15 to 17, wherein the formed UV-absorbing silicone hydrogel contact lens is characterized by having the UVA transmittance of about 20% or less (preferably about 10% or less, more preferably about 5% or less) between 315 and 380 nanometers.

19. The method according to any one of inventions 15 to 17, wherein the formed UV-absorbing silicone hydrogel contact lens is characterized by having a Violet transmittance of about 60% or less (preferably about 50% or less, more preferably about 40% or less, even more preferably about 30% or less) between 380 nm and 440 nm.

20. The method according to any one of inventions 15 to 19, wherein the mold is a reusable mold, wherein the step of irradiating is performed under a spatial limitation of actinic radiation, wherein the formed UV-absorbing silicone hydrogel contact lens comprises a lens edge defined by the spatial limitation of actinic radiation.

21. The method according to any one of inventions 15 to 20, wherein the aqueous lens formulation comprises a water-soluble actinically-crosslinkable prepolymer.

22. The method according to invention 21, wherein water-soluble actinically-crosslinkable prepolymer is: a water-soluble actinically-crosslinkable poly(vinyl alcohol) prepolymer; a water-soluble vinyl group-terminated polyurethane prepolymer; a water-soluble actinically-crosslinkable polyurea prepolymer); a water-soluble actinically-crosslinkable polyacrylamide; a water-soluble actinically-crosslinkable statistical copolymer of vinyl lactam, MMA and a comonomer; a water-soluble actinically-crosslinkable copolymer of vinyl lactam, vinyl acetate and vinyl alcohol; a water-soluble polyether-polyester copolymer with actinically-crosslinkable side chains; a water-soluble branched polyalkylene glycol-urethane prepolymer; a water-soluble polyalkylene glycol-tetra(meth)acrylate prepolymer; a water-soluble actinically-crosslinkable polyallylamine gluconolactone prepolymer, or a mixture thereof.

23. The method according to invention 21 or 22, wherein the aqueous lens formulation comprises from about 15% to about 50% by weight, preferably from about 15% to about 40% by weight, more preferably from about 25% to approximately 40% by weight of the water-soluble actinically-crosslinkable prepolymer.

24. The method of any one of inventions 15 to 23, wherein said at least one UV-absorbing vinylic monomer is selected from the group consisting of: 2-(2-hydroxy-5-vinylphenyl)-2H-benzotriazole; 2-(2-hydroxy-5-acryloxyphenyl)-2H-benzotriazole; 2-(2-hydroxy-3-methacrylamido methyl-5-tert octylphenyl) benzotriazole; 2-(2'-hydroxy-5-methacrylamidophenyl)-5-chlorobenzotriazole; 2-(2'-hydroxy-5'-methacrylamidophenyl)-5-methoxybenzotriazole; 2-(2'-hydroxy-5-methacryloxypropyl-3'-t-butyl-phenyl)-5-chlorobenzotriazole; 2-(2'-hydroxy-5-methacryloxypropylphenyl) benzotriazole; 2-hydroxy-5-methoxy-3-(5-(trifluoromethyl)-2H-benzo[d][1,2,3]triazol-2-yl)benzyl methacrylate (WL-1); 2-hydroxy-5-methoxy-3-(5-methoxy-2H-benzo[d][1,2,3]triazol-2-yl)benzyl methacrylate (WL-5); 3-(5-fluoro-2H-benzo[d][1,2,3]triazol-2-yl)-2-hydroxy-5-methoxybenzyl methacrylate (WL-2); 3-(2H-benzo[d][1,2,3]triazol-2-yl)-2-hydroxy-5-methoxybenzyl methacrylate (WL-3); 3-(5-chloro-2H-benzo[d][1,2,3]triazol-2-yl)-2-hydroxy-5-methoxybenzyl methacrylate (WL-4); 2-hydroxy-5-methoxy-3-(5-methyl-2H-benzo[d][1,2,3]triazol-2-yl)benzyl methacrylate (WL-6); 2-hydroxy-5-methyl-3-(5-(trifluoromethyl)-2H-benzo[d][1,2,3]triazol-2-yl)benzyl methacrylate (WL-7); 4-allyl-2-(5-chloro-2H-benzo[d][1,2,3]triazol-2-yl)-6-methoxyphenol (WL-8); 2-{2'-Hydroxy-3'-tert-5-[3"-(4"-vinylbenzyloxy)propoxy]phenyl}-5-methoxy-2H-benzotriazole; phenol, 2-(5-chloro-2H-benzotriazol-2-yl)-6-(1,1-dimethylethyl)-4-ethenyl- (UVAM); 2-(2'-hydroxy-5-methacryloxyethylphenyl) benzotriazole (2-Propenoic acid, 2-methyl-, 2-[3-(2H-benzotriazol-2-yl)-4-hydroxyphenyl]ethyl ester, Norbloc); 2-{2'-Hydroxy-3'-tert-butyl-5'-[3'-methacryloyloxypropoxy]phenyl}-5-methoxy-2H-benzotriazole (UV13); 2-[2'-Hydroxy-3'-tert-butyl-5'-(3'-acryloyloxypropoxy)phenyl]-5-trifluoromethyl-2H-benzotriazole ($CF_3$—UV13); 2-(2'-hydroxy-5-methacrylamidophenyl)-5-methoxybenzotriazole (UV6); 2-(3-allyl-2-hydroxy-5-methylphenyl)-2H-benzotriazole (UV9); 2-(2-Hydroxy-3-methallyl-5-methylphenyl)-2H-benzotriazole (UV12); 2-3'-t-butyl-2'-hydroxy-5'-(3"-dimethylvinylsilyl-propoxy)-2'-hydroxy-phenyl)-5-methoxybenzotriazole (UV15); 2-(2'-hydroxy-5'-methacryloylpropyl-3'-tert-butyl-phenyl)-5-methoxy-2H-benzotriazole (UV16); 2-(2'-hydroxy-5'-acryloylpropyl-3'-tert-butyl-phenyl)-5-methoxy-2H-benzotriazole (UV16A); 2-[2'-Hydroxy-3'-tert-butyl-5'-(3'-methacryloyloxypropoxy)phenyl]-5-trifluoromethyl-2H-benzotriazole ($CF_3$—UV23), 2-[2'-Hydroxy-3'-tert-butyl-5'-(3'-methacryloyloxypropoxy)phenyl]-5-chloro-2H-benzotriazole (UV28); 2-[2'-Hydroxy-3'-tert-butyl-5'-(3'-acryloyloxypropoxy)phenyl]-5-chloro-2H-benzotriazole; 2-Methylacrylic acid 3-[3-tert-butyl-5-(5-chlorobenzotriazol-2-yl)-4-hydroxyphenyl]-propyl ester (16-100, CAS#96478-15-8); 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9CI) (CAS#83063-87-0); and combinations thereof (preferably from the consisting of: 2-[2'-Hydroxy-3'-tert-butyl-5'-(3'-methacryloyloxypropoxy)phenyl]-5-trifluoromethyl-2H-benzotriazole ($CF_3$—UV23); 2-[2'-Hydroxy-3'-tert-butyl-5'-(3'-methacryloyloxypropoxy)phenyl]-5-chloro-2H-benzotriazole (UV28); 2-[2'-Hydroxy-3'-tert-butyl-5'-(3'-acryloyloxypropoxy)phenyl]-5-chloro-2H-benzotriazole; 2-[2'-Hydroxy-3'-tert-butyl-5'-(3'-acryloyloxypropoxy)phenyl]-5-trifluoromethyl-2H-benzotriazole ($CF_3$—UV13); 2-[3-(2H-benzotriazol-2-yl)-4-hydroxyphenyl]ethyl ester (Norbloc); 2-{2'-Hydroxy-3'-tert-butyl-5'-[3'-methacryloyloxypropoxy]phenyl}-5-methoxy-2H-benzotriazole (UV13); and combinations thereof).

25. The method of any one of inventions 15 to 24, wherein the light source is a light-emitting-device having a peak wavelength of from 400 nm to 480 nm.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Example 1

Transmittance. Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH ~7.0-7.4) as the reference. A UV/visible spectrpohotmeter, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. Transmittance is calculated using the following equations:

$$UVA\ \%\ T = \frac{\text{Average \% T between 380-316 nm}}{\text{Luminescence \% } T} \times 100$$

-continued $$UVB\ \%\ T = \frac{\text{Average }\%\ T\ \text{between 280-315 nm}}{\text{Luminescence }\%\ T} \times 100$$

$$\text{Violet }\%\ T = \frac{\text{Average }\%\ T\ \text{between 440-380 nm}}{\text{Luminescence }\%\ T} \times 100$$

in which Luminescence % T is the average % transmission between 380 and 780.

Photo-Rheology: The photo-rheology experiment measures the elastic (G') and viscous modulus (G") as a function of time during curing. The experiment is conducted by using an appropriate light source, optionally cutoff filters to select wavelengths of interest, and a rheometer. The light source is a Mercury bulb in a Hamamatsu light source. The intensity of light source is set by adjusting the shutter opening to get an appropriate intensity measured by a radiometer. The sample is placed between a quartz plate that allows UV light to pass through and the rheometer. The cure time is determined when the elastic modulus (G') reaches a plateau.

What is claimed is:

1. An acyl germanium photoinitiator of formula (I)

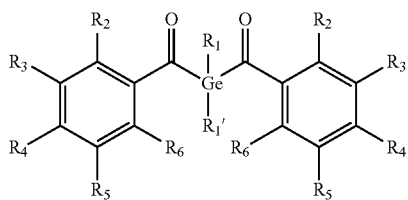

in which:

$R_1$ and $R_1'$ are methyl or ethyl;

one or two of $R_2$, $R_3$, $R_4$, $R_5$, and $R_6$ are a hydrophilic group selected from the group consisting of —$CH_2(OCH_2CH_2)_{n1}$—$OCH_3$, —$CH_2(OCH_2CH_2)_{n1}$—OH, -$L_1$-$SO_3$H,

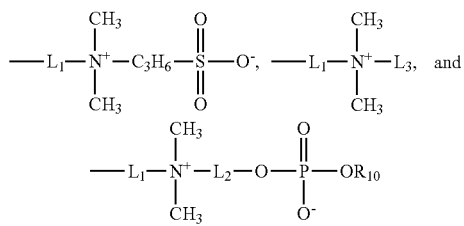

while the others of $R_2$, $R_3$, $R_4$, $R_5$, and $R_6$ independent of one another are hydrogen, methyl, or methoxy, wherein in which n1 is an integer of 4 to 10, $L_1$ is a direct bond or methylene diradical (—$CH_2$—), $L_2$ is ethylene diradical (—$C_2H_4$—) or propylene diradical (—$C_3H_6$—), $L_3$ is hydrogen, methyl or ethyl, $R_{10}$ is methyl or ethyl.

2. The acyl germanium photoinitiator of claim 1, wherein the hydrophilic group is —$CH_2(OCH_2CH_2)_{n1}$—$OCH_3$ or —$CH_2(OCH_2CH_2)_{n1}$—OH.

3. The acyl germanium photoinitiator of claim 1, wherein the hydrophilic group is

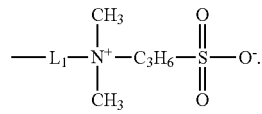

4. The acyl germanium photoinitiator of claim 1, wherein the hydrophilic group is

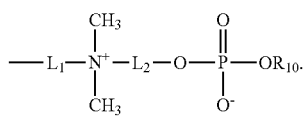

5. The acyl germanium photoinitiator of claim 1, wherein the hydrophilic group is

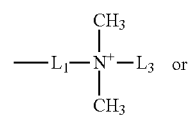

-$L_1$-$SO_3$H.

6. The acyl germanium photoinitiator of claim 1, wherein two of $R_2$, $R_3$, $R_4$, $R_5$, and $R_6$ are a hydrophilic group selected from the group consisting of

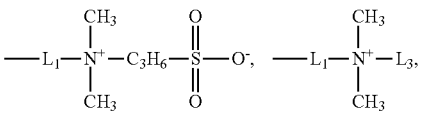
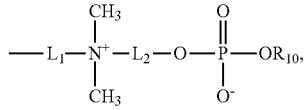

—$CH_2(OCH_2CH_2)_{n1}$—$OCH_3$, —$CH_2(OCH_2CH_2)_{n1}$—OH, and -$L_1$-$SO_3$H while the others of $R_2$, $R_3$, $R_4$, $R_5$, and $R_6$ independent of one another are hydrogen, methyl, or methoxy.

7. The acyl germanium photoinitiator of claim 6, wherein the hydrophilic group is —$CH_2(OCH_2CH_2)_{n1}$—$OCH_3$ or —$CH_2(OCH_2CH_2)_{n1}$—OH.

8. The acyl germanium photoinitiator of claim 6, wherein the hydrophilic group is

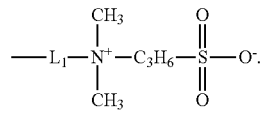

9. The acyl germanium photoinitiator of claim 6, wherein the hydrophilic group is

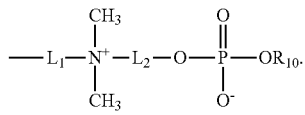

10. The acyl germanium photoinitiator of claim 6, wherein the hydrophilic group is
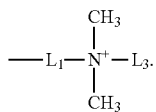
11. The acyl germanium photoinitiator of claim 6, wherein the hydrophilic group is -L$_1$-SO$_3$H.
12. The acyl germanium photoinitiator of claim 1, having a formula selected from the group consisting of formula (I-1) to (I-63):
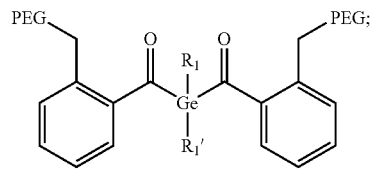 (I-1)
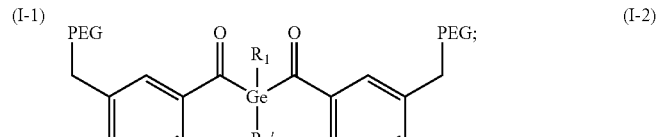 (I-2)
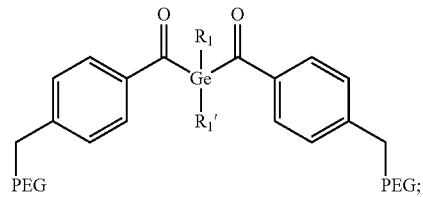 (I-3)
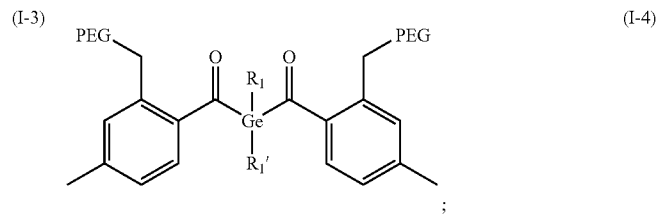 (I-4)
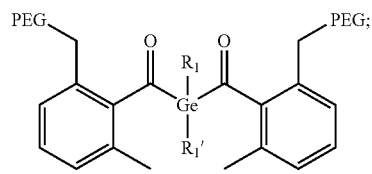 (I-5)
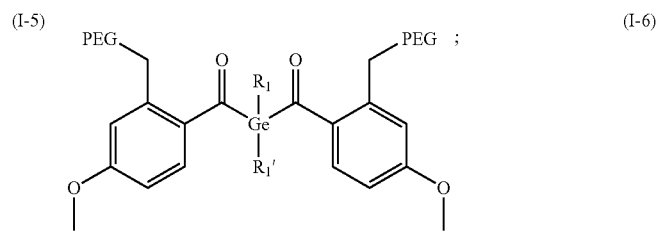 (I-6)
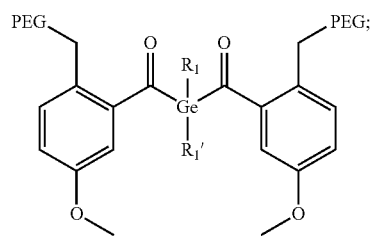 (I-7)
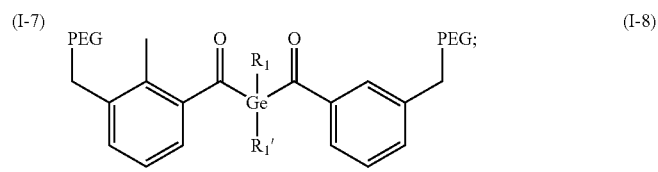 (I-8)
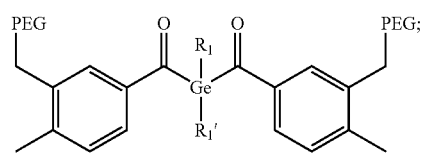 (I-9)
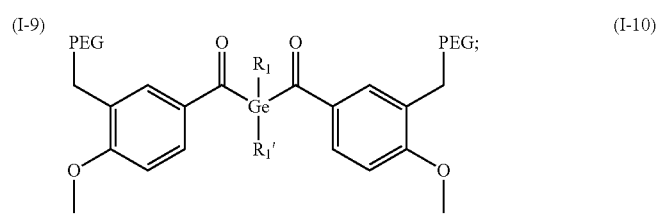 (I-10)
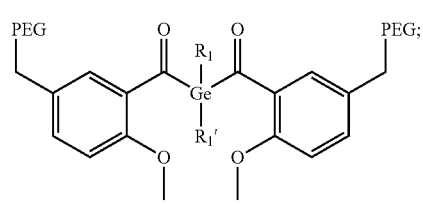 (I-11)
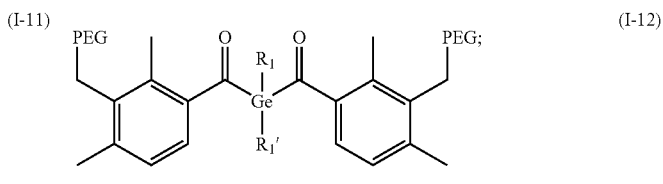 (I-12)

-continued
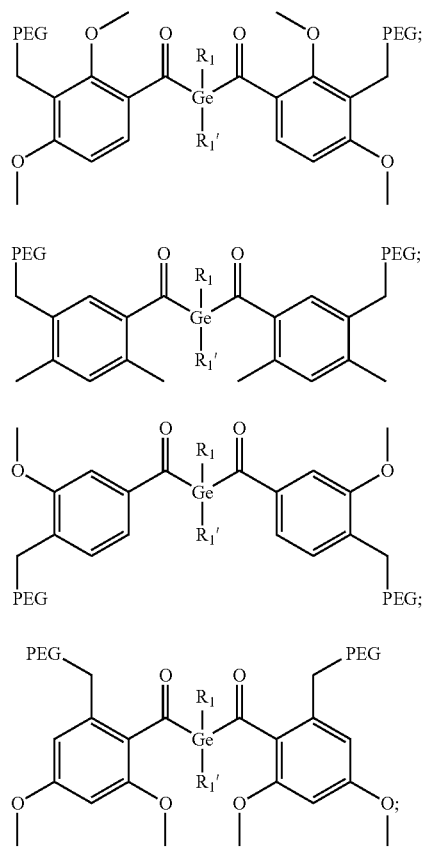
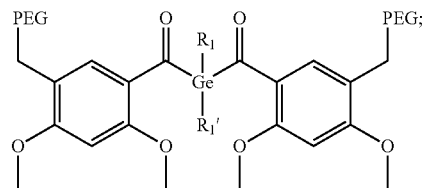
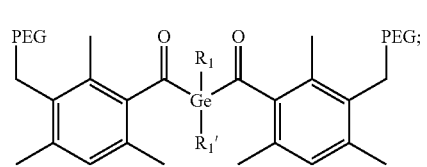
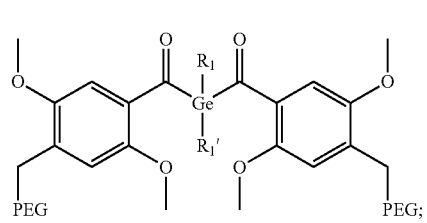
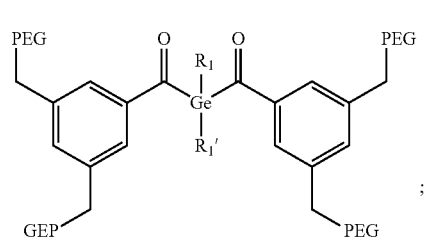
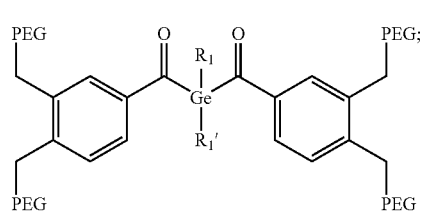
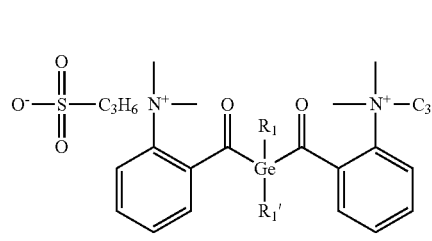
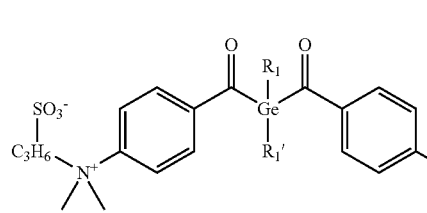

-continued
(I-27)
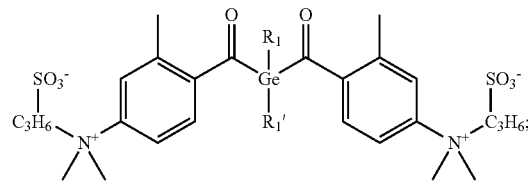
(I-28)
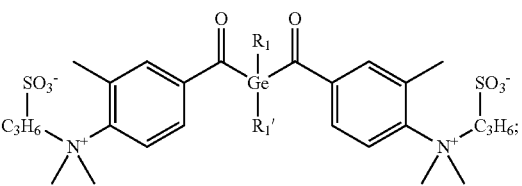
(I-29)
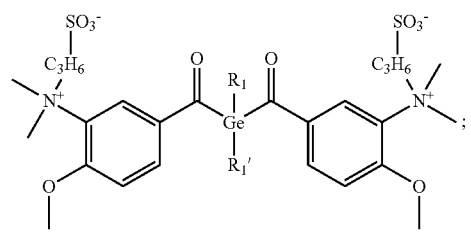
(I-30)
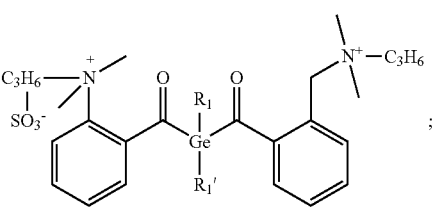
(I-31)
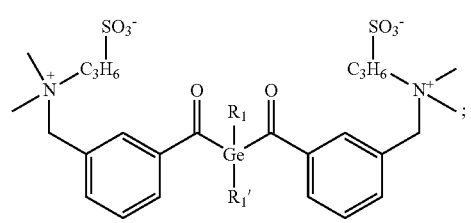
(I-32)
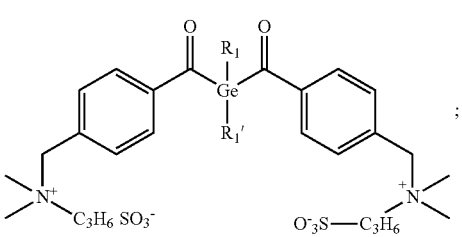
(I-33)
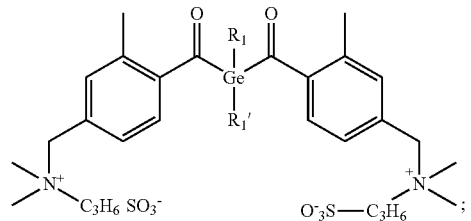
(I-34)
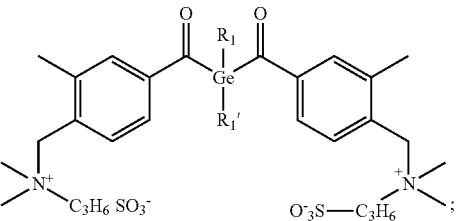
(I-35)
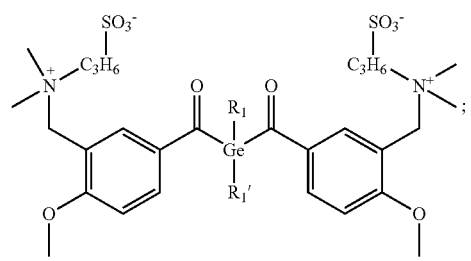
(I-36)
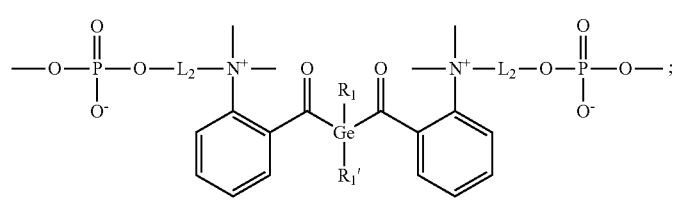
(I-37)
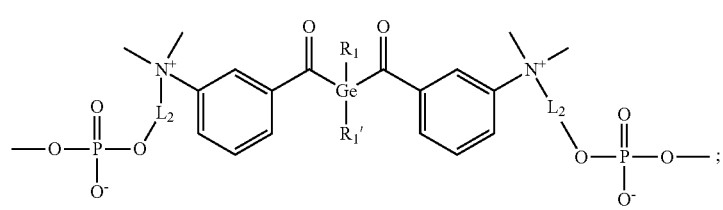

-continued
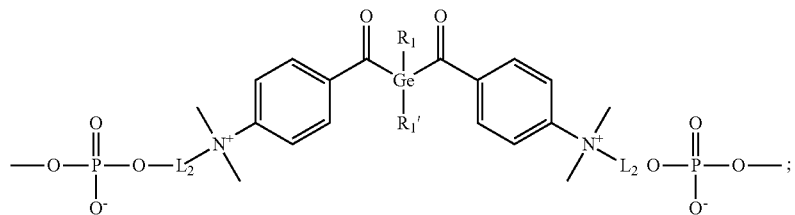
(I-38)
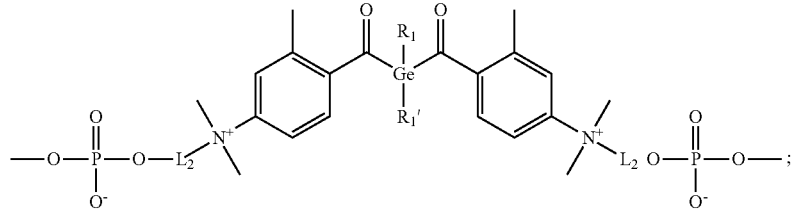
(I-39)
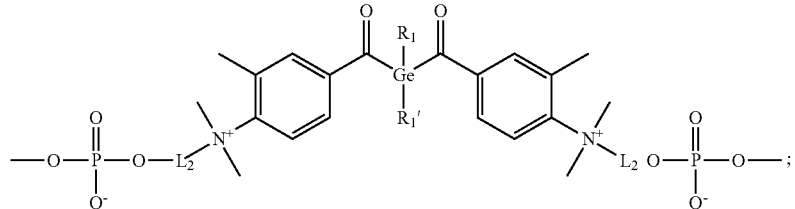
(I-40)
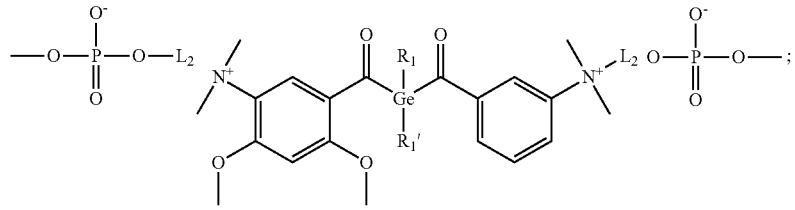
(I-41)
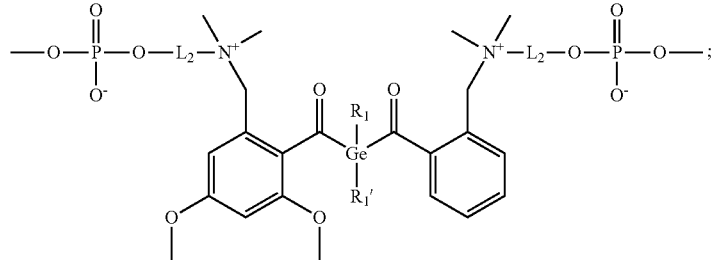
(I-42)
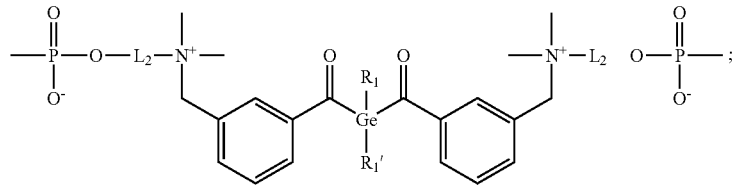
(I-43)
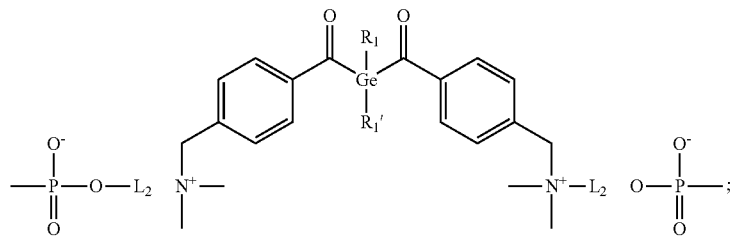
(I-44)

-continued
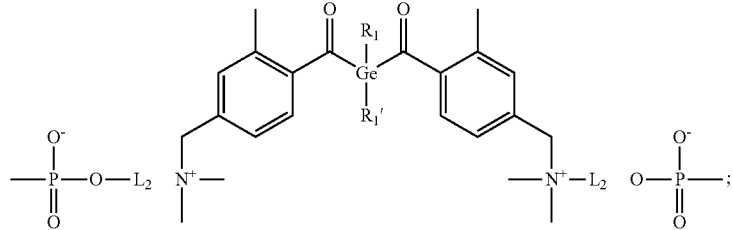 (I-45)
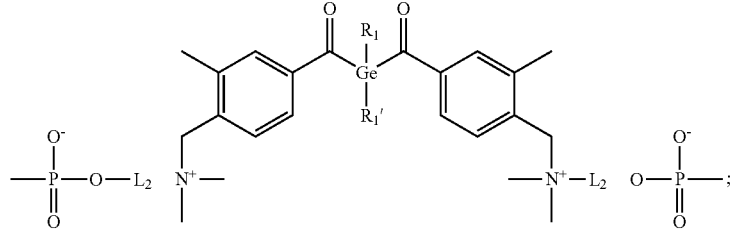 (I-46)
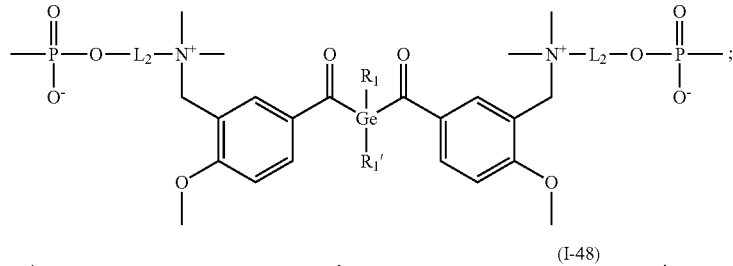 (I-47)
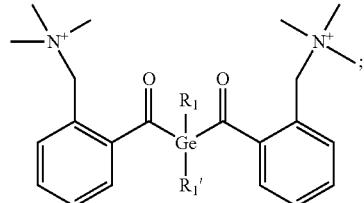 (I-48)
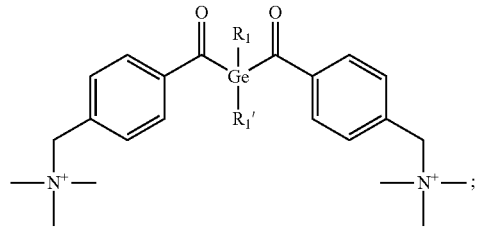 (I-49)
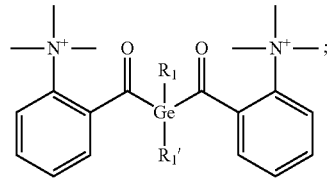 (I-50)
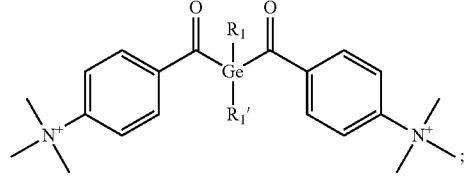 (I-51)
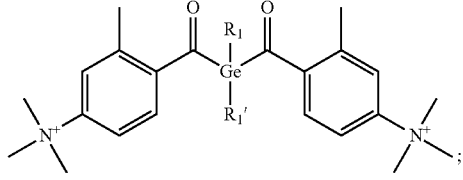 (I-52)
 (I-53)
 (I-54)
 (I-55)

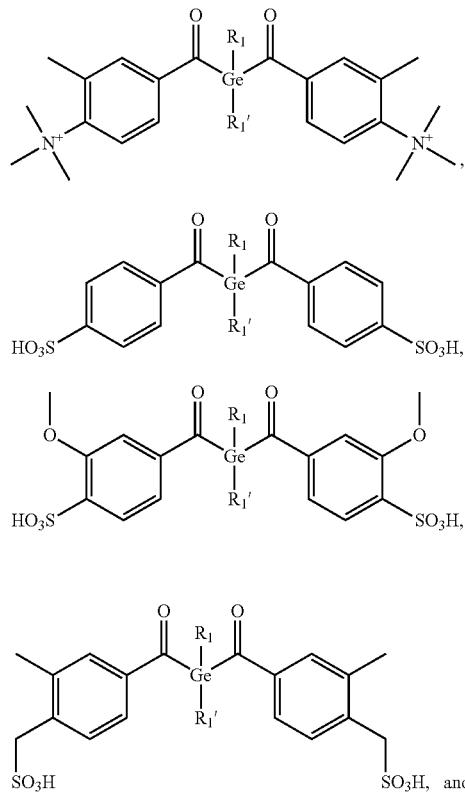

(I-56)
(I-58)
(I-60)
(I-62)

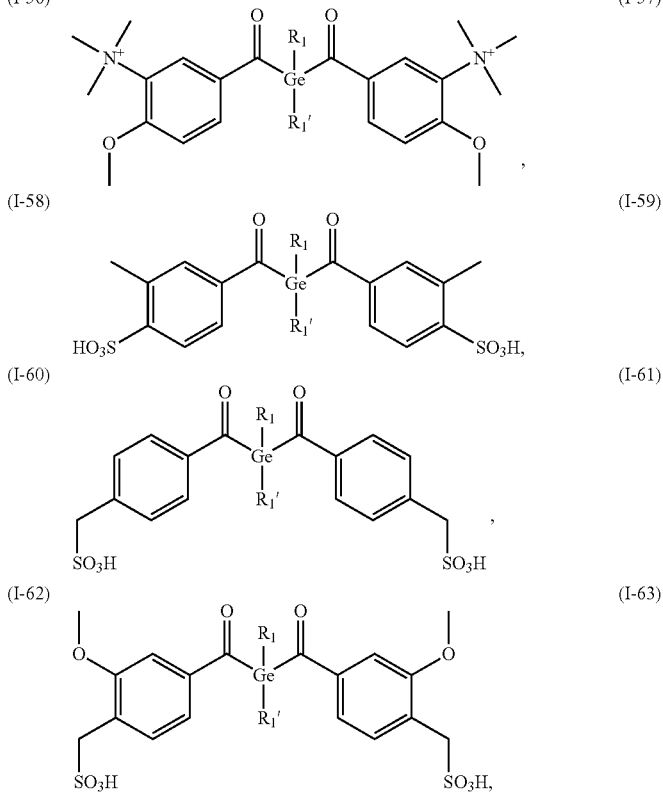

-continued
(I-57)
(I-59)
(I-61)
(I-63)

in which PEG is a monovalent radical of —CH$_2$(OCH$_2$CH$_2$)$_{n1}$—OCH$_3$ or —CH$_2$(OCH$_2$CH$_2$)$_{n1}$—OH in which n1 is an integer of 4 to 10.

13. A method for producing UV-absorbing silicone hydrogel contact lenses, the method comprising the steps of:
(1) obtaining an aqueous lens formulation, wherein the aqueous lens formulation comprises
   (a) from about 0.1% to about 2.0% by weight of at least one acyl germanium photoinitiator of formula (I)

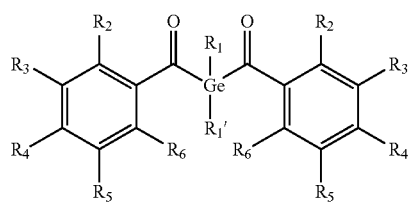

(I)

in which:
R$_1$ and R$_1'$ are methyl or ethyl;
one or two of R$_2$, R$_3$, R$_4$, R$_5$, and R$_6$ are a hydrophilic group selected from the group consisting of —CH$_2$(OCH$_2$CH$_2$)$_{n1}$—OCH$_3$, —CH$_2$(OCH$_2$CH$_2$)$_{n1}$—OH, —L$_1$-SO$_3$H,

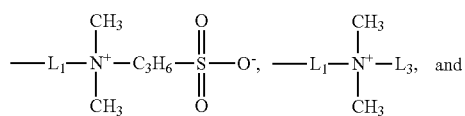

-continued

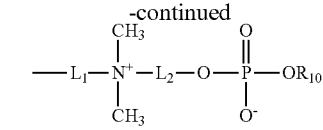

while the others of R$_2$, R$_3$, R$_4$, R$_5$, and R$_6$ independent of one another are hydrogen, methyl, or methoxy, wherein in which n1 is an integer of 4 to 10, L$_1$ is a direct bond or methylene diradical (—CH$_2$—), L$_2$ is ethylene diradical (—C$_2$H$_4$—) or propylene diradical (—C$_3$H$_6$—), L$_3$ is hydrogen or methyl or ethyl, R$_{10}$ is methyl or ethyl, and
   (b) at least one UV-absorbing vinylic monomer or a water-soluble UV-absorbing prepolymer which comprises UV-absorbing moieties attached covalently thereonto or a combination thereof,
(2) introducing the aqueous lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and
(3) irradiating the aqueous lens formulation in the mold by using a light source including a light in a region of from 390 nm to 500 nm, so as to crosslink the lens-forming materials to form the UV-absorbing contact lens, wherein the formed UV-absorbing silicone hydrogel contact lens comprises an anterior surface defined by the first molding surface and an opposite posterior surface defined by the second molding surface and is characterized by having a UVB transmittance of about 10% or less between 280 and 315 nanometers and a UVA transmittance of about 30% or less between 315 and 380 nanometers and and optionally a Violet transmittance of about 60% or less between 380 nm and 440 nm.

14. The method of claim 13, wherein the mold is a reusable mold, wherein the step of irradiating is performed under a spatial limitation of actinic radiation, wherein the formed UV-absorbing silicone hydrogel contact lens comprises a lens edge defined by the spatial limitation of actinic radiation.

15. The method of claim 13, wherein the aqueous lens formulation comprises a water-soluble actinically-crosslinkable prepolymer.

16. The method of claim 15, wherein water-soluble actinically-crosslinkable prepolymer is: a water-soluble actinically-crosslinkable poly(vinyl alcohol) prepolymer; a water-soluble vinyl group-terminated polyurethane prepolymer; a water-soluble actinically-crosslinkable polyurea prepolymer); a water-soluble actinically-crosslinkable polyacrylamide; a water-soluble actinically-crosslinkable statistical copolymer of vinyl lactam, MMA and a comonomer; a water-soluble actinically-crosslinkable copolymer of vinyl lactam, vinyl acetate and vinyl alcohol; a water-soluble polyether-polyester copolymer with actinically-crosslinkable side chains; a water-soluble branched polyalkylene glycol-urethane prepolymer; a water-soluble polyalkylene glycol-tetra(meth)acrylate prepolymer; a water-soluble actinically-crosslinkable polyallylamine gluconolactone prepolymer, or a mixture thereof.

17. The method of claim 16, wherein the aqueous lens formulation comprises from about 15% to about 50% by weight of the water-soluble actinically-crosslinkable prepolymer.

18. The method of claim 13, wherein said at least one UV-absorbing vinylic monomer is selected from the group consisting of: 2-(2-hydroxy-5-vinylphenyl)-2H-benzotriazole; 2-(2-hydroxy-5-acryloxyphenyl)-2H-benzotriazole; 2-(2-hydroxy-3-methacrylamido methyl-5-tert octylphenyl) benzotriazole; 2-(2'-hydroxy-5'-methacrylamidophenyl)-5-chlorobenzotriazole; 2-(2'-hydroxy-5'-methacrylamidophenyl)-5-methoxybenzotriazole; 2-(2'-hydroxy-5'-methacryloxypropyl-3'-t-butyl-phenyl)-5-chlorobenzotriazole; 2-(2'-hydroxy-5'-methacryloxypropylphenyl) benzotriazole; 2-hydroxy-5-methoxy-3-(5-(trifluoromethyl)-2H-benzo[d][1,2,3]triazol-2-yl)benzyl methacrylate (WL-1); 2-hydroxy-5-methoxy-3-(5-methoxy-2H-benzo[d][1,2,3]triazol-2-yl) benzyl methacrylate (WL-5); 3-(5-fluoro-2H-benzo[d][1,2,3]triazol-2-yl)-2-hydroxy-5-methoxybenzyl methacrylate (WL-2); 3-(2H-benzo[d][1,2,3]triazol-2-yl)-2-hydroxy-5-methoxybenzyl methacrylate (WL-3); 3-(5-chloro-2H-benzo[d][1,2,3]triazol-2-yl)-2-hydroxy-5-methoxybenzyl methacrylate (WL-4); 2-hydroxy-5-methoxy-3-(5-methyl-2H-benzo [d][1,2,3]triazol-2-yl)benzyl methacrylate (WL-6); 2-hydroxy-5-methyl-3-(5-(trifluoromethyl)-2H-benzo[d][1,2,3]triazol-2-yl)benzyl methacrylate (WL-7); 4-allyl-2-(5-chloro-2H-benzo[d][1,2,3]triazol-2-yl)-6-methoxyphenol (WL-8); 2-{2'-Hydroxy-3'-tert-5'[3"-(4"-vinylbenzyloxy)propoxy]phenyl}-5-methoxy-2H-benzotriazole; phenol, 2-(5-chloro-2H-benzotriazol-2-yl)-6-(1,1-dimethylethyl)-4-ethenyl- (UVAM); 2-(2'-hydroxy-5'-methacryloxyethylphenyl) benzotriazole (2-Propenoic acid, 2-methyl-, 2-[3-(2H-benzotriazol-2-yl)-4-hydroxyphenyl] ethyl ester, Norbloc); 2-{2'-Hydroxy-3'-tert-butyl-5'-[3'-methacryloyloxypropoxy]phenyl}-5-methoxy-2H-benzotriazole (UV13); 2-[2'-Hydroxy-3'-tert-butyl-5'-(3'-acryloyloxypropoxy)phenyl]-5-trifluoromethyl-2H-benzotriazole (CF$_3$-UV13); 2-(2'-hydroxy-5'-methacrylamidophenyl)-5-methoxybenzotriazole (UV6); 2-(3-allyl-2-hydroxy-5-methylphenyl)-2H-benzotriazole (UV9); 2-(2-Hydroxy-3-methallyl-5-methylphenyl)-2H-benzotriazole (UV12); 2-3'-t-butyl-2'-hydroxy-5'-(3"-dimethylvinylsilylpropoxy)-2'-hydroxy-phenyl)-5-methoxybenzotriazole (UV15); 2-(2'-hydroxy-5'-methacryloylpropyl-3'-tert-butyl-phenyl)-5-methoxy-2H-benzotriazole (UV16); 2-(2'-hydroxy-5'-acryloylpropyl-3'-tert-butyl-phenyl)-5-methoxy-2H-benzotriazole (UV16A); 2-[2'-Hydroxy-3'-tert-butyl-5'-(3'-methacryloyloxypropoxy)phenyl]-5-trifluoromethyl-2H-benzotriazole (CF$_3$-UV23), 2-[2'-Hydroxy-3'-tert-butyl-5'-(3'-methacryloyloxypropoxy)phenyl]-5-chloro-2H-benzotriazole (UV28); 2-[2'-Hydroxy-3'-tert-butyl-5'-(3'-acryloyloxypropoxy)phenyl]-5-chloro-2H-benzotriazole; 2-Methylacrylic acid 3-[3-tert-butyl-5-(5-chlorobenzotriazol-2-yl)-4-hydroxyphenyl]-propyl ester (16-100, CAS#96478-15-8); 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9CI) (CAS#83063-87-0); and combinations thereof.

19. The method of claim 18, wherein the light source is a light-emitting-device having a peak wavelength of from 400 nm to 480 nm.

20. The method of claim 13, wherein the light source is a light-emitting-device having a peak wavelength of from 400 nm to 480 nm.

* * * * *